(12) United States Patent
Herold et al.

(10) Patent No.: US 11,684,670 B2
(45) Date of Patent: Jun. 27, 2023

(54) METHODS OF USING HSV-2 SINGLE CYCLE VIRUS DELTA-GD AND HSV-2 RECOMBINANT GLYCOPROTEIN D

(71) Applicant: Albert Einstein College of Medicine, Bronx, NY (US)

(72) Inventors: Betsy C. Herold, Rowayton, CT (US); Clare Burn Aschner, Bronx, NY (US)

(73) Assignee: ALBERT EINSTEIN COLLEGE OF MEDICINE, Bronx, NY (US)

( * ) Notice: Subject to any disclaimer, the term of this patent is extended or adjusted under 35 U.S.C. 154(b) by 0 days.

(21) Appl. No.: 17/335,548

(22) Filed: Jun. 1, 2021

(65) Prior Publication Data

US 2021/0369838 A1 Dec. 2, 2021

Related U.S. Application Data

(60) Provisional application No. 63/031,816, filed on May 29, 2020.

(51) Int. Cl.
| | |
|---|---|
| *A61K 39/245* | (2006.01) |
| *A61P 31/22* | (2006.01) |
| *A61K 9/00* | (2006.01) |
| *C12N 7/00* | (2006.01) |
| *A61K 39/00* | (2006.01) |

(52) U.S. Cl.
CPC .......... *A61K 39/245* (2013.01); *A61K 9/0019* (2013.01); *A61P 31/22* (2018.01); *C12N 7/00* (2013.01); *A61K 2039/54* (2013.01); *C12N 2710/16621* (2013.01); *C12N 2710/16622* (2013.01); *C12N 2710/16634* (2013.01)

(58) Field of Classification Search
CPC .. A61K 39/245; A61K 39/12; A61K 2039/54; A61K 2039/5254; A61K 2039/5256; A61K 2039/525; A61K 2039/572; C07K 14/005; C12N 7/00; C12N 2710/16621; C12N 2710/16622; C12N 2710/16643; C12N 2710/16671; A61P 37/04; A61P 31/22; A61P 17/02

See application file for complete search history.

(56) References Cited

FOREIGN PATENT DOCUMENTS

| CN | 104694553 B | 4/2018 |
|---|---|---|
| WO | 2013173590 A1 | 11/2013 |
| WO | 2015134368 A2 | 9/2015 |
| WO | 2020081820 A1 | 4/2020 |

OTHER PUBLICATIONS

Aschner CB. Mechanisms of Protection Induced by a Single Cycle HSV-2 Candidate Vaccine Deleted in Glycoprotein D. Doctoral Thesis, Albert Einstein College of Medicine. Public Defense: Feb. 28, 2020; ProQuest Doc. ID: 2395778918. (Year: 2020).*
International Search Report dated Sep. 22, 2021; International Application No. PCT/US2021/035168; International Filing Date Jun. 1, 2021 (9 pgs).
Written Opinion dated Sep. 22, 2021; International Application No. PCT/US2021/035168; International Filing Date Jun. 1, 2021 (12 pgs).
Aschner, et al., "Model of vaccine efficacy against HSV-2 superinfection of HSV-1 seropositive mice demonstrates protection by antibodies mediating cellular cytotoxicity" npj Vaccines, 2020, (5:35, pp. 1-8.
Belshe et al. "Efficacy results of a trial of a herpes simplex vaccine" New England Journal of Medicine, 366(1), Jan. 5, 2012, pp. 34-43.
Belshe, et al., "Serum Antibody Responses after Intradermal Vaccination against Influenza" The New England Journal of Medicine, 2004, vol. 351, pp. 2286-2294.
Bernard, et al., "Immunogenicity, Protective Efficacy, and Non-Replicative Status of the HSV-2 Vaccine Candidate HSV529 in Mice and Guinea Pigs" PLoS ONE, 2015, 10.1371 e0121518 (21 pgs).
Bryan, et al. "Low-Dose Intradermal and Intramuscular Vaccination against Hepatitis B" Clinical Infectious Diseases 1992, vol. 14 pp. 697-707.
Burn, et al., "A Herpes Simplex Virus (HSV)-2 Single-Cycle Candidate Vaccine Deleted in Glycoprotein D Protects Male Mice from Lethal Skin Challenge With Clinical Isolates of HSV-1 and HSV-2" Journal of Infectious Diseases 2018, vol. 217, pp. 754-758.
Cook, et al., "Reactogenicity and immunogenicity of an inactivated influenza vaccine administered by intramuscular or subcutaneous injection in elderly adults" Vaccine, 2006, vol. 24, pp. 2395-2402.
Da Costa et al.; "Immunization against Genital Herpes with a Vaccine Virus That has Defects in Productive and Latent Infection", Proceedings of the National Academy of Sciences of the United States of America, Jun. 8, 1999, vol. 96, pp. 6994-6998.
Da Costa, et al., "Comparison of Different Forms of Herpes Simplex Replication-Defective Mutant Viruses as Vaccines in a Mouse Model of HSV-2 Genital Infection" Virology, 2001, vol. 288, pp. 256-263.
Da Costa, et al., "Construction, Phenotypic Analysis, and Immunogenicity of a UL5/UL29 Double Deletion Mutant of Herpes Simplex Virus 2" Journal of Virology, 2000, vol. 74, No. 17, pp. 7963-7971.
Delagrave, et al., "Immunogenicity and Efficacy of Intramuscular Replication-Defective and Subunit Vaccines against Herpes Simplex Virus Type 2 in the Mouse Genital Model" PLoS ONE, 2012, vol. 7, issue 10, e46714 (9 pgs).

(Continued)

*Primary Examiner* — Rachel B Gill
(74) *Attorney, Agent, or Firm* — Cantor Colburn LLP

(57) ABSTRACT

Methods of vaccinating, immunizing and/or treating a subject against a herpes simplex virus infection or a disease caused by a herpes simplex virus infection comprise administering to the subject an effective amount of a HSV-2 single-cycle virus and an effective amount of a recombinant HSV-2 glycoprotein D, wherein the HSV-2 single-cycle virus comprises HSV-2 having a deletion of glycoprotein D-encoding gene in the genome and the HSV-2 is phenotypically complemented with an HSV-1 glycoprotein D on a lipid bilayer of the HSV-2.

30 Claims, 18 Drawing Sheets

Specification includes a Sequence Listing.

(56) References Cited

OTHER PUBLICATIONS

Diaz, et al., "Intramuscular delivery of replication-defective herpes simplex virus gives antigen expression in muscle syncytia and improved protection against pathogenic HSV-2 strains", Virology, 2018, vol. 513, pp. 129-135).
Dropulic, et al., "A Randomized, Double-Blinded, Placebo-Controlled, Phase 1 Study of a Replication-Defective Herpes Simplex Virus (HSV) Type 2 Vaccine, HSV529, in Adults With or Without HSV Infection" Journal of Infectious Diseases, 2019, vol. 220, pp. 990-1000).
Dubois, et al., "Dendritic cells directly modulate B cell growth and differentiation" Journal of Leukocyte Biology, 1999, vol. 66, pp. 224-230.
Dudek, et al., "Evidence for Differences in Immunologic and Pathogenesis Properties of Herpes Simplex Virus 2 Strains From the United States and South Africa" Journal of Infectious Diseases 2011, vol. 203, pp. 1434-1441.
Gillet, et al., "Immunogenicity and safety of concomitant administration of a measles, mumps and rubella vaccine (M-M-RvaxPro) and a varicella vaccine (VARIVAX) by intramuscular or subcutaneous routes at separate injection sites: a randomised clinical trial" BMC Med, 2009, 7:16, 11 pgs.
Hoshino, et al., "Comparative Efficacy and Immunogenicity of Replication-Defective, Recombinant Glycoprotein, and DNA Vaccines for Herpes Simplex Virus 2 Infections in Mice and Guinea Pigs." Journal of Virology 2005, vol. 79, No. 1, 410-418.
Hoshino, et al., "Comparison of immunogenicity and protective efficacy of genital herpes vaccine candidates herpes simplex virus 2 dl5-29 and dl5-29-41L in mice and guinea pigs" Vaccine 2008, vol. 26, pp. 4034-4040.
Hoshino, et al., "Protection from Herpes Simplex Virus (HSV)-2 Infection with Replication-Defective HSV-2 or Glycoprotein D2 Vaccines in HSV-1-Seropositive and HSV-1-Seronegative Guinea Pigs" Journal of Infectious Diseases 2009, vol. 200, pp. 1088-1095.
Kao, et al., "Murine Model of Maternal Immunization Demonstrates Protective Role for Antibodies That Mediate Antibody-Dependent Cellular Cytotoxicity in Protecting Neonates From Herpes Simplex Virus Type 1 and Type 2" Journal of Infectious Diseases 2020, vol. 221, pp. 729-738.
Lafferty, et al., "Herpes simplex virus type 1 as a cause of genital herpes: impact on surveillance and prevention" Journal of Infectious Diseases 2000, vol. 181. pp 1454 1457.
Laurent, et al., "Safety and efficacy of novel dermal and epidermal microneedle delivery systems for rabies vaccination in healthy adults" Vaccine 2010, vol. 28, pp. 5850-5856.
Ligas, et al., "A Herpes Simples Virus Mutant in Which Glycoprotein D Sequences Are Replaced by β-Galactosidase Sequences Binds to but is Usable to Penetrate into Cells" Journal of Virology, May 1988, vol. 62, No. 5 pp. 1486-1494.

Looker, et al., "Global Estimates of Prevalent and Incident Herpes Simplex Virus Type 2 Infections in 2012" PLoS ONE 2015, 10.1371 e114989 (23 pgs).
Namvar, et al., "Detection and Typing of Herpes Simplex Virus (HSV) in Mucocutaneous Samples by TaqMan PCR Targeting a GB Segment Homologous for HSV Types 1 and 2" Journal of Clinical Microbiology 2005, vol. 43, pp. 2058-2064.
Peng, et al., "T-bet regulates IgG class switching and pathogenic autoantibody production" Proc. Natl. Acad. Sci. U.S.A. 2002, vol. 99, No. 8 (5545-5550).
Petro, et al., "Herpes simplex type 2 virus deleted in glycoprotein D protects against vaginal, skin and neural disease" Elife 2015, 4:e06054 (18 pages).
Petro, et al., "HSV-2 ΔgD elicits FcγR-effector antibodies that protect against clinical isolates" JCI Insight Aug. 4, 2016; vol. 1 (12):e88529.
Rahman, et al., "Cellular and Humoral Immune Responses Induced by Intradermal or Intramuscular Vaccination With the Major Hepatitis B Surface Antigen" Hepatology 2000, vol. 31, pp. 521-527.
Ramsey, et al., "A Single-Cycle Glycoprotein D Deletion Viral Vaccine Candidate, ΔgD-2, Elicits Polyfunctional Antibodies That Protect against Ocular Herpes Simplex Virus" Journal of Virollgy 2020, vol. 94, Issue 13 (12 pgs).
Roberts, et al., "Increasing Proportion of Herpes Simplex Virus Type 1 as a Cause of Genital Herpes Infection in College Students" American Sexually Transmitted Diseases Association 2003, vol. 30, pp. 797-800.
Romani, et al., Targeting skin dendritic cells to improve intradermal vaccination) Current Topics in Microbiology and Immunology 2012, vol. 351, pp. 113-138.
Sattentau, Q., "Avoiding the void: cell-to-cell spread of human viruses" National Reviews Microbiology 2008, vol. 6, pp. 815-826.
Stanberry, et al., "Glycoprotein-D-adjuvant vaccine to prevent genital herpes" The New England Journal of Medicine 2002, vol. 347, pp. 1652-1661.
Van Damme, et al., "Safety and efficacy of a novel microneedle device for dose sparing intradermal influenza vaccination in healthy adults" Vaccine 2009, vol. 27, pp. 454-459.
Wahl, et al., "Intradermal, Subcutaneous or Intramuscular Administration of Hepatitis B Vaccine: Side Effects and Antibody Response" Scandinavian Journal of Infectious Diseases 1987, vol. 19, pp. 617-621.
Xu, et al., "Trends in Herpes Simplex Virus Type 1 and Type 2 Seroprevalence in the United States" JAMA 2006, vol. 296, pp. 964-973.
Morello, C. et al.; "Immunization with Herpes Simplex Virus 2 (HSV-2) Genes plus Inactivated HSV-2 is Highly Protective against Acute and Recurrent HSV-2 Disease"; Journal of Virology, vol. 85, Issue No. 7; 2011; pp. 3461-3472; DOI: 10.1128/JV1.02521-10.
Zhang, P. et al.; "A Herpes Simplex Virus 2 (HSV-2) Glycoprotein D expressing Nonreplicating Dominant-Negative HSV-2 Virus Vaccine is Superior to a gD2 Subunit Vaccine against HSV-2 Genital Infection in Guinea Pigs"; PLoS One, vol. 9, Issue No. 6; 2014; pp. 1-9; DOI: 10.1371/journal.pone.0101373.

* cited by examiner

METHODS OF USING HSV-2 SINGLE CYCLE VIRUS DELTA-GD AND HSV-2 RECOMBINANT GLYCOPROTEIN D

CROSS-REFERENCE TO RELATED APPLICATION

This application claims the benefit of U.S. Provisional Application No. 63/031,816 filed on May 29, 2020, which is incorporated herein by reference in its entirety.

FEDERAL RESEARCH STATEMENT

This invention was made with government support under grant numbers R01 AI17321-01 and AI057552 awarded by the National Institutes of Health, NIAID. The government has certain rights in the invention.

BACKGROUND

Herpes simplex virus 1 (HSV-1) and herpes simplex virus 2 (HSV-2) are prevalent human pathogens. HSV-1 infects approximately 67% of the population by 49 years of age and is the primary cause of oral and ocular disease, a leading cause of infectious corneal blindness and fatal infectious encephalitis, and has emerged as the more common cause of genital disease in the developed world (Looker, K. J. et al., *PLoS ONE* 2015, 10, e114989-23; Lafferty, W. E. et al, *Journal of Infectious Diseases* 2000, 181, 1454-1457; Roberts, C. M. et al, *Sexually Transmitted Diseases* 2003, 30, 797-800; Xu, F. et al., *JAMA* 2006, 296, 964-973). HSV-2 is estimated to over 400 million people worldwide, is the primary cause of genital disease in the developing world and a major risk factor for HIV acquisition and transmission (Looker, K. J. et al., *PLoS ONE* 2015, 10, e114989-23).

The enormous global health burden of these two related viruses has resulted in extensive vaccine development efforts, which have primarily focused on the generation of neutralizing antibodies (nAbs) targeting the viral envelope glycoproteins D (gD) as the correlate of immune protection. One such vaccine was a recombinant gD-2 protein vaccine formulated with a proprietary aluminum hydroxide (alum) and monophosphoryl lipid A adjuvant, gD-2-AS04 (GlaxoSmithKline). Despite promising preclinical studies and a Phase 3 clinical trial of serodiscordant couples demonstrating protection in HSV-1 and HSV-2 doubly seronegative women (but not men), a subsequent field trial found no protection against HSV-2 infection or disease in doubly-seronegative women (Stanberry, L. R, et al, *N Engl J Med* 2002, 347, 1652-1661; Belshe, R. B., et al., *N Engl J Med* 2012, 366, 34-43). The vaccine was administered intramuscularly at 0, 1 and 6 months. Another vaccine that has recently completed Phase I clinical trials is a replication-defective HSV-2 strain deleted in two genes involved in viral replication (UL5 and UL29), designated dl5-29 (HSV529, Sanofi Pasteur) (Dropulic, L. K., et al, *Journal of Infectious Diseases* 2019, 220, 990-1000). In preclinical studies, the vaccine was safe, induced nAb and T cell responses and reduced the establishment of latency in the peripheral nerves (Da Costa, X. J. E. A., et al., *J. Virol.* 2000, 74, 7963-7971; Da Costa, X. J. E. A., et al., *Virology* 2001, 288, 256-263; Hoshino, Y., et al., *Vaccine* 2008, 26, 4034-4040; Hoshino, Y., et al., *J. Virol.* 2004, 79, 410-418; Hoshino, Y., et al. *Journal of Infectious Diseases* 2009, 200, 1088-1095; Bernard, M.-C., et al., *PLoS ONE* 2015, 10, e0121518-21). The Phase I study also found that the vaccine was safe and elicited a >4-fold increase in nAb responses in HSV sero-negative participants, but no sustained increase in nAb responses in seropositive participants. Moreover, only a subset of participants elicited significant CD4 and even fewer CD8 T cell responses (Dropulic, L. K., et al., *Journal of Infectious Diseases* 2019, 220, 990-1000).

A single-cycle HSV-2 strain deleted in glycoprotein D (ΔgD-2) has been developed to generate a single-cycle candidate HSV-2 vaccine strain designated ΔgD-2. In pre-clinical murine studies, this vaccine strain, ΔgD-2, elicited high-titer non-neutralizing Abs that activate Fc gamma receptors (FcγRs) to induce antibody-dependent cell-mediated cytotoxicity (ADCC). Two doses administered subcutaneously completely protected female and/or male mice against lethal vaginal or skin challenge with clinical isolates of HSV-1 and HSV-2 and prevented the establishment of latency (Petro, C., et al., eLife 2015; Petro, C. D., et al, *JCI Insight* 2016, 1, 1-15; Burn, C., et al., *Journal of Infectious Diseases* 2017, 1-5; Kao, C. M., et al., *Journal of Infectious Diseases* 2019, 42, 47-10). Moreover, vaccination of female mice protected their pups from subsequent HSV challenge in the first week of life (Kao, C. M., et al., *Journal of Infectious Diseases* 2019, 42, 47-10). In contrast to adjuvanted recombinant gD, ΔgD-2 boosted the total and the ADCC Ab responses in HSV-1 seropositive mice and prevented subsequent lethal HSV-2 superinfection (Burn Aschner, C., et al., *npj Vaccines* 2020, 1-33).

Additional strategies for preventing and treating infection and disease caused by HSV-1 and/or HSV-2 would be beneficial.

BRIEF DESCRIPTION

A method of vaccinating a subject against a herpes simplex virus-2 (HSV-2) infection or a disease caused by an HSV-2 infection comprising administering to the subject an effective amount of an HSV-2 single-cycle virus and an effective amount of a recombinant HSV-2 glycoprotein D to vaccinate the subject for the HSV-2 infection or the disease caused by the HSV-2 infection, wherein the HSV-2 single-cycle virus comprises HSV-2 having a deletion of glycoprotein D-encoding gene in the genome and the HSV-2 is phenotypically complemented with an HSV-1 glycoprotein D on a lipid bilayer of the HSV-2.

A method of immunizing a subject against herpes simplex virus-2 (HSV-2) infection or a disease caused by an HSV-2 infection comprising administering to the subject an effective amount of an HSV-2 single-cycle virus and an effective amount of a recombinant HSV-2 glycoprotein D to immunize the subject for the HSV-2 infection or the disease caused by the HSV-2 infection, wherein the HSV-2 single-cycle virus comprises HSV-2 having a deletion of glycoprotein D-encoding gene in the genome and the HSV-2 is phenotypically complemented with an HSV-1 glycoprotein D on a lipid bilayer of the HSV-2.

A method of treating or preventing an HSV-2 infection in a subject or treating or preventing a disease caused by an HSV-2 infection in a subject, comprising administering to the subject an effective amount of an HSV-single-cycle virus 2 and an effective amount of a recombinant HSV-2 glycoprotein D to treat or prevent the HSV-2 infection or the disease caused by the HSV-2 infection in the subject, wherein the HSV-2 single-cycle virus comprises HSV-2 having a deletion of glycoprotein D-encoding gene in the genome and the HSV-2 is phenotypically complemented with an HSV-1 glycoprotein D on a lipid bilayer of the HSV-2.

The above described and other features are exemplified by the following figures and detailed description.

BRIEF DESCRIPTION OF THE DRAWINGS

The following figures are exemplary embodiments wherein the like elements are numbered alike.

(FIGS. 4C-D) Gating strategy is shown for the assessment of CD4 and CD8 T cell activation (FIGS. 4A-B). Data was analyzed by Mixed Effects Analysis, *p<0.5, p<0.01, *p<0.001, ****p<0.0001; n=5 mice pergroup.

DETAILED DESCRIPTION

Figure 1A:
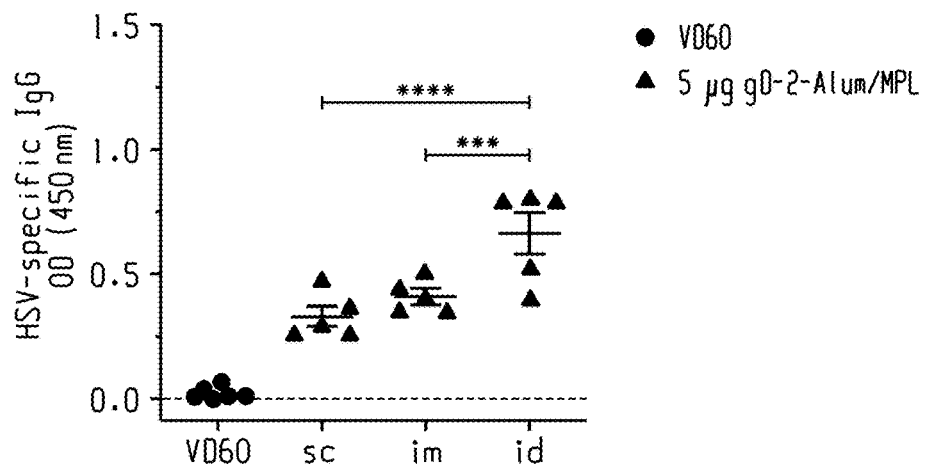
FIGS. 1A-1I. Immunogenicity of viral and adjuvanted subunit HSV vaccines is modulated by vaccination route. Female C57BL/6 mice were vaccinated twice, three weeks apart with $5 \times 10^4$, $5 \times 10^5$ or $5 \times 10^6$ pfu/mouse of dl5-29 or ΔgD-2 or 5 μg gD-2-Alum/MPL subcutaneously (sc), intramuscularly (im) or intradermally (id). One week following the second immunization, mice were retro-orbitally bled and serum was tested for (FIGS. 1A-C) total HSV-specific IgG by ELISA, (FIGS. 1D-F) neutralization titer and (FIGS. 1G-I) FcγRIV activation by NFAT-luciferase reporter assay. N=5 mice per group for gD-2-Alum/MPL and dl5-29 in a single experiment; n=5 mice per group, two independent experiments for ΔgD-2. Asterisks denote significance, *p<0.05, p<0.01, *p<0.001, ****p<0.0001 by ANOVA.

Vaccine immunogenicity is impacted by how the viral antigens are presented by the vaccine (attenuated, replication-defective, single-cycle, inactivated virus, or adjuvanted subunit protein), as well as the dose and route of administration. The immunization route is often based on pragmatic rather than immunologic considerations.

The immunogenicity and efficacy of the genetically modified, single-cycle, herpes simplex virus-2 (HSV-2) having a deletion of glycoprotein D in the genome (ΔgD-2), using different routes and vaccine doses was studied and compared with dl5-29 and recombinant HSV-2 glycoprotein D (rgD-2) adjuvanted with alum and monophosphoryl lipid A (MPL) (rgD-2-Alum/MPL), which is similar to the gD-2-AS04 vaccine (GlaxoSmithKline). The immunogenicity and efficacy of simultaneous administration of ΔgD-2 and the rgD-2 was also evaluated. It has been surprisingly discovered that co-administration of ΔgD-2 and recombinant HSV-2 glycoprotein D (rgD-2) does not interfere with the immunogenicity of either vaccine. In particular, administration of adjuvanted rgD-2 and a relatively low dose of ΔgD-2 delivered simultaneously to the same or opposite flank does not interfere with the immunogenicity of either vaccine and is more protective than the adjuvanted rgD-2 alone. Further, it has been shown that the combination of low dose ΔgD-2 with rgD-2 provides additive protection.

As used herein, "therapeutically effective amount" or "effective amount" or "amount effective" refers to a quantity of a specific substance sufficient to achieve a desired effect in a subject.

"Treat" or "treating," means to administer a vaccine of the disclosure or a product of the disclosure to a subject or patient having one or more disease symptoms, or being suspected of having a disease, for which the vaccine or product has therapeutic activity or prophylactic activity. The vaccine or product can be administered in an amount effective to alleviate one or more disease symptoms in the treated subject, whether by inducing the regression of or inhibiting the progression of such symptom(s) by any clinically measurable degree. The terms further includes a postponement of development of the symptoms associated with a disorder and/or a reduction in the severity of the symptoms of such disorder. The terms further include ameliorating existing uncontrolled or unwanted symptoms, preventing additional symptoms, and ameliorating or preventing the underlying causes of such symptoms.

"Preventing" means administering an amount of a vaccine of the disclosure or a product of the disclosure sufficient to significantly reduce the likelihood of a disease from occurring in a subject who may be predisposed to the disease but who does not have it. In the context of viral infection "preventing" includes administering an amount of the vaccine or an immune product resulting from administration of the vaccine to a subject known to be at enhanced risk of viral infection.

The term "adjuvant" as used herein means any component added to a vaccine that augments, enhances and/or boosts the immune response to an antigen, but when the administered alone does not generate an immune response.

Disclosed herein are methods of vaccinating, immunizing and/or treating a subject against a herpes simplex virus (HSV) infection. Disclosed herein also are methods of vaccinating, immunizing, and/or treating a subject against a disease caused by an HSV infection. The HSV infection is a herpes simplex virus-2 (HSV-2) infection, a herpes simplex virus-1 (HSV-1) infection, or a HSV-1 and HSV-2 co-infection. In an aspect, the HSV infection is a herpes simplex virus-2 (HSV-2) infection. The disease caused by HSV-1 infection, HSV-2 infection, or HSV-1 and HSV-2 co-infection includes herpes, oral herpes, herpes whitlow, genital herpes (genital ulcer), eczema herpeticum, herpes gladiatorum, HSV keratitis, HSV retinitis, HSV encephalitis or HSV meningitis. In an aspect, the disease caused by the HSV infection is a genital ulcer.

The methods disclosed herein comprise administering to the subject an effective amount of an HSV-2 single-cycle virus and an effective amount of a recombinant HSV-2 glycoprotein D (rgD-2). The HSV-2 single-cycle virus is an HSV-2 having a deletion of the HSV-2 glycoprotein D-encoding gene in the genome and the HSV-2 is phenotypically complemented with an HSV-1 glycoprotein D on a lipid bilayer of the HSV-2. The HSV-2 glycoprotein D-encoding gene is the Us6 gene of HSV-2, and is either fully or partially deleted in the HSV-2 genome. In an aspect, the HSV-2 glycoprotein D-encoding gene is fully deleted in the HSV-2 genome.

The HSV-1 glycoprotein D is not encoded for by the HSV-2 genome. In particular, the HSV-2 having the deletion of HSV-2 glycoprotein D is phenotypically complemented with the HSV-1 glycoprotein D by propagating the HSV-2 having the deletion of the HSV-2 glycoprotein D-encoding gene in a cell which has been transfected to express the HSV-1 gD. A complete description of the HSV-2 single-cycle virus is found in WO 2015/134368, which is incorporated herein by reference.

The HSV-2 single-cycle virus having a deletion of the HSV-2 glycoprotein D-encoding gene in the genome of the HSV-2, and which is phenotypically complemented with the HSV-1 glycoprotein D by propagating the HSV-2 in a complementing cell expressing the HSV-1 glycoprotein D, is referred to herein interchangeably as "HSV-2 ΔgD-2" or "ΔgD-2" or "HSV-2 single-cycle virus".

The recombinant HSV-2 glycoprotein D is referred to herein interchangeably as "rgD-2" or "recombinant HSV-2 gD" or "recombinant gD-2."

In aspects, the recombinant HSV-2 gD is combined with an adjuvant, and the adjuvanted recombinant HSV-2 gD is administered to the subject.

The type of adjuvant is not limited, and can be any adjuvant capable of augmenting, enhancing, and/or boosting the immune response of the subject to the recombinant HSV-2 gD relative to administration of non-adjuvanted recombinant HSV-2 gD (e.g., soluble recombinant HSV-2 gD). Non-limiting examples of an adjuvant include alum, potassium aluminum sulfate, aluminum hydroxide, aluminum hydroxy phosphate sulfate (AAHS), aluminum phosphate, calcium phosphate hydroxide, squalene, plant saponins from Quillaja (e.g., Quil A™), soybean, or *Polygala senega*, monophosphoryl lipid A (MPL), Freund's adjuvant (complete or incomplete), an oil in water emulsion containing a non-metabolizable oil, paraffin oil (e.g., EMULSIGEN™, MVP Laboratories, Ralston, Nebr.), mineral oil, plant or vegetable oil, squalane or squalene (e.g. MF59™), and/or animal oil, CpG oligodeoxynucleotides (ODN), QS-21, or a combination thereof. Adjuvants can be used with or without other specific immunostimulating agents such as 3-DMP, polymeric or monomeric amino acids such as polyglutamic acid or poly(lysine), or other immunopotentiating agents.

Disclosed herein are methods of vaccinating a subject against herpes simplex virus-1 (HSV-1) infection, herpes simplex virus-2 (HSV-2) infection, or an HSV-1 and HSV-2 co-infection. Also disclosed are methods of vaccinating a subject against a disease caused by HSV-1 infection, HSV-2 infection, or HSV-1 and HSV-2 co-infection. A method of vaccinating a subject against an HSV-1 infection, an HSV-2 infection, or an HSV-1 and HSV-2 co-infection or a disease caused by HSV-1 infection, HSV-2 infection, or HSV-1 and HSV-2 co-infection, comprises administering to the subject an effective amount of the recombinant HSV-2 single-cycle virus and an effective amount of the recombinant HSV-2 glycoprotein D to vaccinate the subject for the HSV-2 infection, the HSV-1 infection, or the HSV-1 and HSV-2 co-infection. The HSV-2 single-cycle virus comprises HSV-2 having a deletion of glycoprotein D-encoding gene in the genome and the HSV-2 is phenotypically complemented with an HSV-1 glycoprotein D on a lipid bilayer of the HSV-2.

In an aspect, a method of vaccinating a subject against herpes simplex virus-2 (HSV-2) infection or a disease caused by an HSV-2 infection comprises administering to the subject an effective amount of the HSV-2 single-cycle virus and an effective amount of the recombinant HSV-2 gD to vaccinate the subject for the HSV-2 infection or the disease caused by the HSV-2 infection.

In an aspect, a method of vaccinating a subject against HSV-1 infection or a disease caused by the HSV-1 infection comprises administering to the subject an effective amount of the HSV-2 single-cycle virus and an effective amount of the recombinant HSV-2 gD to vaccinate the subject for the HSV-1 infection or the disease caused by the HSV-1 infection.

In an aspect, a method of vaccinating a subject against an HSV-1 and HSV-2 co-infection or a disease caused by HSV-1 and HSV-2 co-infection comprises administering to the subject an effective amount of the HSV-2 single-cycle virus and an effective amount of the recombinant HSV-2 gD effective to vaccinate the subject for the HSV-1 and HSV-2 coinfection or the disease caused by the HSV-1 and HSV-2 co-infection.

Also disclosed herein are methods of immunizing a subject against herpes simplex virus-1 (HSV-1) infection, herpes simplex virus-2 (HSV-2) infection, or an HSV-1 and HSV-2 co-infection, as well as methods of immunizing a subject against a disease caused by HSV-1 infection, HSV-2 infection, or HSV-1 and HSV-2 co-infection. A method of immunizing a subject against a herpes simplex virus-1 (HSV-1) infection, a herpes simplex virus-2 (HSV-2) infection, or an HSV-1 and HSV-2 co-infection or a disease caused by HSV-1 infection, HSV-2 infection, or HSV-1 and HSV-2 co-infection, comprises administering to the subject an effective amount of the recombinant HSV-2 single-cycle virus and an effective amount of the recombinant HSV-2 glycoprotein D to immunize the subject for the HSV-2 infection, the HSV-1 infection, or the HSV-1 and HSV-2 co-infection or the disease caused by HSV-1 infection, HSV-2 infection, or HSV-1 and HSV-2 co-infection. The HSV-2 single-cycle virus comprises HSV-2 having a deletion of glycoprotein D-encoding gene in the genome and the HSV-2 is phenotypically complemented with an HSV-1 glycoprotein D on a lipid bilayer of the HSV-2.

In an aspect, a method of immunizing a subject against HSV-2 infection or a disease caused by the HSV-2 infection comprises administering to the subject an effective amount of the recombinant HSV-2 single-cycle virus and an effective amount of the recombinant HSV-2 glycoprotein D to immunize the subject for the HSV-2 infection or the disease caused by the HSV-2 infection.

Disclosed herein also are methods of preventing or treating an HSV-2 infection, an HSV-1 infection, or an HSV-2 and HSV-1 co-infection in a subject. Also disclosed are methods of preventing or treating a disease caused by an HSV-2 infection, an HSV-1 infection, or an HSV-2 and HSV-1 co-infection in a subject.

A method of preventing or treating an HSV-2 infection, an HSV-1 infection, or an HSV-2 and HSV-1 co-infection in a subject comprises administering to the subject an effective amount of the HSV-2 single-cycle virus and an effective amount of the recombinant HSV-2 glycoprotein D to treat the subject for the HSV-2 infection, the HSV-1 infection, or the HSV-2 and HSV-1 co-infection. A method of preventing or treating a disease caused by an HSV-2 infection, an HSV-1 infection, or an HSV-2 and HSV-1 co-infection in a subject comprises administering to the subject an amount of the HSV-2 single-cycle virus and an amount of the recombinant HSV-2 glycoprotein D effective to treat the subject for the HSV-2 disease caused by the HSV-2 infection, the HSV-1 infection, or the HSV-2 and HSV-1 co-infection. The HSV-2 single-cycle virus comprises HSV-2 having a deletion of glycoprotein D-encoding gene in the genome and the HSV-2 is phenotypically complemented with an HSV-1 glycoprotein D on a lipid bilayer of the HSV-2.

In an aspect, a method of treating or preventing a herpes simplex virus-2 (HSV-2) infection in a subject or treating a disease caused by an HSV-2 infection in a subject, comprises administering to the subject an effective amount of the HSV-2 single-cycle virus and an effective amount of a recombinant HSV-2 glycoprotein D to treat the subject for the HSV-2 infection.

In aspects, the disclosed methods of vaccinating, immunizing, and/or treating a subject comprise administering an effective amount of a composition, a pharmaceutical formulation, or a vaccine comprising the HSV-2 single-cycle virus and administering an effective amount of a composition, a pharmaceutical formulation or a vaccine comprising the recombinant HSV-2 gD.

In aspects, the administering of the HSV-2 single-cycle virus and the recombinant HSV-2 glycoprotein D occurs at substantially the same time. As used herein, "substantially the same time" refers to administration of the HSV-2 single-cycle virus and the recombinant HSV-2 gD within a short period of time of one another, for example, 1 second to 24 hours, 1 second to 12 hours, 1 second to 8 hours, 1 second to 4 hours, 1 second to 2 hours (120 minutes), 1 second to one hour (60 minutes), or 1 second to 30 minutes.

In an aspect, the administering of the HSV-2 single-cycle virus occurs 1 second to 60 minutes before the administering of the recombinant glycoprotein D.

In an aspect, the administering of the HSV-2 single-cycle virus occurs 1 second to 60 minutes after the administering of the recombinant glycoprotein D.

In an aspect, the administering of the HSV-2 single-cycle virus and the recombinant HSV-2 gD occurs simultaneously, e.g., at the same time. As used herein, simultaneous administration or administering simultaneously refer to instances in which there is no discernible time between the administering of the HSV-2 single-cycle virus and the recombinant HSV-2 gD.

A composition or pharmaceutical formulation or vaccine comprising the HSV-2 single-cycle virus and a composition or pharmaceutical formulation or vaccine comprising the recombinant HSV-2 gD can be administered to the subject. The composition or pharmaceutical composition or vaccine comprising the HSV-2 single-cycle virus and/or the recombinant HSV-2 gD are formulated for administration to the subject.

In an aspect, the HSV-2 single-cycle virus and the recombinant HSV-2 gD are present in different compositions, pharmaceutical formulations or vaccines for separate administration to the subject. In other words, the HSV-2 single-cycle virus and the recombinant HSV-2 gD are not present in the same composition, pharmaceutical formulation or vaccine. However, the disclosure is not necessarily limited thereto, and a composition, pharmaceutical formulation or vaccine including both the HSV-2 single-cycle virus and the recombinant HSV-2 gD may be used as long as the viability of the HSV-2 single-cycle virus is not compromised by any of the materials present therein.

In an aspect of the present disclosure, the HSV-2 single-cycle virus and the recombinant HSV-2 gD are formulated for separate administration to the subject and are administered to the subject at substantially the same time. In an aspect, the administering of the HSV-2 single-cycle virus occurs 1 second to 60 minutes before the administering of the recombinant gD. In an aspect, the administering of the HSV-2 single-cycle virus occurs 1 second to 60 minutes after the administering of the recombinant gD.

In an aspect, the HSV-2 single-cycle virus and the recombinant HSV-2 gD are formulated for separate administration to the subject and are administered to the subject simultaneously. For example, a composition, pharmaceutical formulation or vaccine comprising the HSV-2 single-cycle virus and a composition, pharmaceutical formulation or vaccine comprising the recombinant HSV-2 gD can be combined together prior to administration to the subject and administered simultaneously. Or for example, a composition, pharmaceutical formulation or vaccine comprising the HSV-2 single-cycle virus and a composition, pharmaceutical formulation or vaccine comprising the recombinant HSV-2 gD can be administered to the subject by separate means (e.g., different syringes) at the same time.

In aspects, a composition, pharmaceutical formulation or vaccine comprising the HSV-2 single-cycle virus or the recombinant HSV-2 gD is formulated so that it is suitable for administration to a human subject. In particular, the composition or pharmaceutical formulation or vaccine is formulated to be suitable for the intended route of administration to a subject. The intended route of administration of the composition, pharmaceutical formulation or vaccine comprising the HSV-2 single-cycle virus can be the same as or different from the intended route of administration of the composition, pharmaceutical formulation or vaccine comprising the recombinant HSV-2 gD. In an aspect, the HSV-2 single-cycle virus and the recombinant HSV-2 gD are independently formulated for the same route of administration. In an aspect, the HSV-2 single-cycle virus and the recombinant HSV-2 gD are formulated for the different routes of administration.

In an aspect, the composition, pharmaceutical formulation or vaccine is formulated so that it is suitable for subcutaneous, intramuscular, intradermal, or intravaginal administration to a subject. In the methods disclosed herein, and in the compositions or pharmaceutical formulations or vaccines disclosed herein, administration can be auricular, buccal, conjunctival, cutaneous, subcutaneous, endocervical, endosinusial, endotracheal, enteral, epidural, via hemodialysis, interstitial, intrabdominal, intraamniotic, intra-arterial, intra-articular, intrabiliary, intrabronchial, intrabursal, intracardiac, intracartilaginous, intracaudal, intracavernous, intracavitary, intracerebral, intracisternal, intracorneal, intracoronary, intradermal, intradiscal, intraductal, intraepidermal, intraesophagus, intragastric, intravaginal, intragingival, intraileal, intraluminal, intralesional, intralymphatic, intramedullary, intrameningeal, intramuscular, intraocular, intraovarian, intraepicardial, intraperitoneal, intrapleural, intraprostatic, intrapulmonary, intrasinal, intraspinal, intrasynovial, intratendinous, intratesticular, intrathecal, intrathoracic, intratubular, intratumor, intratympanic, intrauterine, intravascular, intravenous, intraventricular, intravesical, intravitreal, laryngeal, nasal, nasogastric, ophthalmic, oral, oropharyngeal, parenteral, percutaneous, periarticular, peridural, rectal, inhalationally, retrobulbar, subarachnoid, subconjuctival, sublingual, submucosal, topically, transdermal, transmucosal, transplacental, transtracheal, ureteral, urethral, or vaginal. A combination comprising at least one of the foregoing routes of administration can also be used.

In an aspect, the composition, pharmaceutical formulation or vaccine including the HSV-2 single-cycle virus and the composition, pharmaceutical formulation or vaccine including the recombinant HSV-2 gD are formulated for subcutaneous, intramuscular or intradermal administration by injection. The composition, pharmaceutical formulation or vaccine including the HSV-2 single-cycle virus can be administered in a same region or a different region as the composition, pharmaceutical formulation or vaccine including the recombinant HSV-2 gD. For example, the HSV-2 single-cycle virus and the recombinant HSV-2 gD can be each be administered to the same or different limbs.

The compositions, pharmaceutical formulations, or vaccines disclosed herein can comprise an adjuvant. In an aspect, a composition, pharmaceutical formulation, or vaccine comprising the HSV-2 single cycle virus or the recombinant HSV-2 gD comprises an adjuvant. The compositions, pharmaceutical formulations, or vaccines disclosed herein can also include a pharmaceutically acceptable carrier.

As used herein, "pharmaceutically acceptable" means a substance approved by a regulatory agency of the Federal or a state government or listed in the U.S. Pharmacopoeia, other generally recognized pharmacopoeia in addition to other formulations that are safe for use in animals, and more particularly in humans and/or non-human mammals. The term "pharmaceutically acceptable carrier" refers to an excipient, diluent, preservative, solubilizer, emulsifier, adjuvant (also referred to as immunological adjuvant), and/or vehicle with which the present antibody or fragment is administered. Examples of pharmaceutically acceptable carriers include, but are not limited to, phosphate buffered saline solution, sterile water (including water for injection USP), emulsions such as oil/water emulsion, and various types of wetting agents. Preferred diluents for aerosol or parenteral administration are phosphate buffered saline or normal (0.9%) saline, for example 0.9% sodium chloride solution, USP. Compositions comprising such carriers are formulated by well-known conventional methods (see, for example, Remington's Pharmaceutical Sciences, 18th edition, A. Gennaro, ed., Mack Publishing Co., Easton, Pa., 1990; and Remington, The Science and Practice of Pharmacy 20th Ed. Mack Publishing, 2000, the content of each of which is hereby incorporated in its entirety). In non-limiting examples, the carrier comprises one or more of dibasic sodium phosphate, potassium chloride, monobasic potassium phosphate, polysorbate 80 (e.g. 2-[2-[3,5-bis(2-hydroxyethoxy)oxolan-2-yl]-2-(2-hydroxyethoxy)ethoxy]ethyl (E)-octadec-9-enoate), disodium edetate dehydrate, sucrose, monobasic sodium phosphate monohydrate, and dibasic sodium phosphate dihydrate. The pharmaceutically acceptable carrier is not limited as long as it is not incompatible with the viability of the HSV-2 single cycle virus or the stability and/or conformation of the recombinant HSV-2 gD.

In an aspect, a composition, pharmaceutical formulation, or vaccine comprising the recombinant HSV-2 gD can comprise a stabilizer to prevent loss of activity or structural integrity of the protein due to the effects of denaturation, oxidation or aggregation over a period of time during storage and transportation prior to use. The composition, pharmaceutical formulation, or vaccine can further comprise a salt, a surfactant, a pH and/or tonicity agent, or a combination thereof.

Where the composition, pharmaceutical formulation, or vaccine is used as an injection, a pH value is in an approximately neutral pH range (a pH or 6.8 to 7.4). In an aspect, the composition, pharmaceutical formulation, or vaccine is in liquid form. In an aspect, the composition or pharmaceutical composition is isotonic.

In the present disclosure, the subject is a subject in need of treatment or prevention of an HSV-2 infection, an HSV-1 infection, or an HSV-2 and HSV-1 co-infection. The subject can also be a subject in need of treatment or prevention of a disease caused by an HSV-2 infection, an HSV-1 infection, or an HSV-2 and HSV-1 co-infection. The subject is a mammalian subject. For example, the subject is a human subject. The HSV-2 single cycle virus and recombinant HSV-2 gD can be formulated for administration to a human subject.

The methods disclosed herein induce an immune response in the subject, which elicits antibodies, cellular immune responses, and/or other immune factors (e.g., complement) that minimize and/or prevent viral dissemination and/or viral infection in the subject. In particular, the immune response comprises the production of antibodies that activate Fc receptors (FcR-activating antibody) to mediate an antibody-dependent cellular cytotoxicity (ADCC) response. In an aspect, the administration of an effective amount of the HSV-2 single-cycle virus elicits the production of FcR-activating antibody (also referred to as antibody dependent cellular cytotoxicity (ADCC) antibody). The effective amount of HSV-2 single-cycle virus is an amount of plaque forming units (pfu) of the HSV-2 single-cycle virus which achieves the stated aim.

This disclosure is further illustrated by the following examples, which are non-limiting.

EXAMPLES

Materials and Methods

Age-matched female C57BL/6 (BL/6) mice were purchased from the Jackson Laboratory (JAX, Bar Harbor, Me.).

Vero (Green Monkey Kidney cells line, ATCC), VD60 (Ligas, M. W., et al, *J. Virol.* 1988, 62, 1486-1494) and V5-29 (Da Costa, X. J. E. A., et al., *Proc. Natl. Acad. Sci. U.S.A.* 1999, 96, 6994-6998) cells were grown in DMEM (Invitrogen, Carlsbad, Calif.) supplemented with 10% FBS (Hyclone, Logan, Utah) and 1% penicillin-streptomycin (Invitrogen). The clinical isolates used for viral challenges included HSV-2 (SD90) (Dudek, T. E., et al., *Journal of Infectious Diseases* 2011, 203, 1434-1441) and HSV-2 (4674). HSV-2 strain 4674 was obtained from the Montefiore Clinical Virology Lab (Petro, C. D., et al, *JCI Insight* 2016, 1, 1-15; Burn, C., et al, *Journal of Infectious Diseases* 2017, 1-5). The viral isolates were propagated and titered on Vero cells (Petro, C. D., et al., *JCI Insight* 2016, 1, 1-15).

ΔgD-2 was propagated in complementing VD60 cells, and titered both on the VD60 and Vero cells (Petro, C., et al., eLife 2015; Petro, C. D., et al, *JCI Insight* 2016, 1, 1-15; Burn, C., et al., *Journal of Infectious Diseases* 2017, 1-5; Kao, C. M., et al., *Journal of Infectious Diseases* 2019, 42, 47-10). D/5-29 was propagated on complementing V5-29 cells (Da Costa, X. J. E. A., et al., *J. Virol.* 2000, 74, 7963-7971) and was also titered on complementing and non-complementing Vero cells. Recombinant gD-2 protein (5 µg) was provided by the Einstein Macromolecular Therapeutics Development Facility and adjuvanted with 150 µg alum (Imject Alum, Pierce Biotechnology, Rockland, Ill.) and 12.5 µg MPL (Invivogen, San Diego, Calif.) (rgD-2/Alum-MPL) (Burn, C., et al., *Journal of Infectious Diseases* 2017, 1-5). The recombinant gD-2 is substantially the same as the recombinant gD-2 used in the AS04 vaccine (GlaxoSmithKline).

Vaccination and Challenge Protocol

Female C57BL/6 mice were vaccinated subcutaneously, intramuscularly or intradermally (two doses administered at three-week intervals) with $5 \times 10^4$, $5 \times 10^5$ or $5 \times 10^6$ pfu ΔgD-2 or dl5-29 (based on viral titer on complementing cell line); 5 µg of rgD-2/Alum-MPL; or a combination of $5 \times 10^4$ pfu ΔgD-2 and 5 µg of rgD-2/Alum-MPL. For intradermal vaccinations, a specialist intradermal microneedle designed for use in mice was used (Nanopass, Nes Ziona, ISR). Three weeks after the second vaccine dose, mice were challenged on the skin with a 10×lethal dose for 90% of animals (LD90) of HSV-2 SD90 (Petro, C., et al., eLife 2015). Mice were monitored daily for epithelial and neurological disease and scored as described. For skin disease: 1) erythema at inoculation site; 2) spread to distant site, zosteriform lesions, edema; 3) ulceration, epidermal spread, limb paresis; 4) hind limb paralysis and 5) death. Mice were euthanized at a score of 4 and assigned a score of 5 the following day.

ELISA for HSV-Specific Antibodies

Total or isotype-specific HSV-binding IgG was measured by ELISA using recombinant monoclonal antibodies or serum collected one week following the second dose of vaccine. ELISA plates were coated with lysates of Vero cells infected with HSV-2 (G) at an MOI of 0.1 for 24 hours or uninfected Vero cell lysates as control. Serial dilutions of serum in duplicate were incubated with coated plates overnight at 4° C., and bound IgG was quantified using biotin-labeled secondary Abs (BD Pharmingen, CA). Background binding to uninfected Vero cell lysates was subtracted from binding to HSV-infected Vero cell lysates to quantify HSV-specific binding.

FcγR Activation Assay

Fc-receptor activation, and more specifically FcγRIV activation, was determined using the murine FcγRIV ADCC Reporter Bioassay (Promega, Madison, Wis.) (Petro, C. D., et al, *JCI Insight* 2016, 1, 1-15; Burn, C., et al., *Journal of Infectious Diseases* 2017, 1-5). Target Vero cells were infected with HSV-2 (SD90) at an MOI of 0.1 for 12 hours. Infected or uninfected control cells were transferred to white, flat-bottomed 96-well plates and incubated with heat-inactivated serum from vaccinated or control immunized mice; or human serum samples (see below) (1:5 dilution in DMEM) for 15 minutes at room temperature. Murine FcγRIV were added for 6 hours at 37° C. 5% $CO_2$ and FcγRIV activation was detected by the addition of luciferin substrate. Plates were read in a SpectraMax M5$^e$ (Molecular Devices). Fold induction was calculated relative to luciferase activity in the absence of serum Neutralization Assay Neutralizing titers were determined by plaque reduction assay (Petro, C., et al, eLife 2015; Petro, C. D., et al, *JCI Insight* 2016, 1, 1-15; Burn, C., et al., *Journal of Infectious Diseases* 2017, 1-5). Serial 2-fold dilutions of heat-inactivated serum in duplicate were incubated with virus (50 pfu/well) for 1 hour at 37° C. and then applied to Vero cell monolayers for 1 hour at 37° C. Cells were fixed with methanol and stained with Giemsa after a 48-h incubation. Plaques were counted and the neutralization titer was defined as the highest dilution to result in a 50% reduction in plaque numbers.

Quantification of Viral DNA in Neuronal Tissue by Quantitative PCR

At the time of euthanasia (when mice succumbed to disease or day 14 post-HSV-2 challenge); sacral nerve tissue was extracted and DNA was isolated using the Qiagen Blood and Tissue DNA isolation kit (Qiagen). 10 ng of DNA per sample was loaded and primers and probes specific for HSV-2 gB were used to quantify HSV DNA (HSV-2 forward primer (SEQ ID NO: 1) sequence 5'-TGCAGTT-TACGTATAACCACATACAGC-3' (SEQ ID NO: 1); HSV-2 reverse primer sequence 5'-AGCTTGCGGGCCTCGTT-3' (SEQ ID NO: 2); HSV-2 probe sequence 5'-CGCCCCAG-CATGTCGTTCACGT-3' (SEQ ID NO: 3) (Namvar, L., et al., *Journal of Clinical Microbiology* 2005, 43, 2058-2064). Mouse β actin was used as a loading control (Applied Biosystems, Foster City, Calif.), and qPCR was run in an Applied Biosystems QuantStudio 7 Flex. Based on a standard curve, this assay consistently detected copy numbers greater than or equal to 4. Samples with fewer than 4 copies detected were considered negative (Petro, C., et al, *eLife* 2015; Petro, C. D., et al, *JCI Insight* 2016, 1, 1-15; Burn, C., et al., *Journal of Infectious Diseases* 2017, 1-5).

Cell Isolation and Flow Cytometry

Peripheral blood was collected by retro-orbital bleed, pipetted into 5 ml pre-warmed ACK lysing buffer (Lonza BioWhittaker) and incubated for 7 minutes at 37° C. Following lysis, cells were washed 2× in PBS without calcium and magnesium. For splenocyte isolation, spleens were isolated from vaccinated animals and mechanically digested by pressing through a 70 µm cell strainer. Cells were pelleted by centrifugation and resuspended in 2 ml ACK lysing buffer. After 7 minutes at 37° C., RPMI was added and cells were pelleted by centrifugation. Cells were subsequently washed and resuspended in RPMI for further processing.

For ex-vivo stimulation, $2\times10^6$ splenocytes per 200 μL of RPMI+10% FBS were plated in a U-bottom 96-well plate. Cells were treated with PHA (5 μg/mL) or $1\times10^6$ PFU UV-inactivated HSV-2 SD90 and incubated at 37° C. for 18 hours. Brefeldin A (BioLegend, San Diego, Calif.) was added for the final 5 hours of stimulation. For UV inactivation of virus, HSV-2 SD90 was diluted in RPMI in a 24-well dish and exposed to a hand-held UV light positioned 4 inches above the plate for 30 minutes. Cells were then processed for extra- and intracellular staining for flow cytometry.

For flow cytometry analysis, $1\times10^6$ to $2\times10^6$ cells per 100 μL were incubated with Zombie Near-IR fixable viability dye and TruStain FcX (anti-mouse CD16/CD32) antibody for 10 minutes at room temperature. For surface staining, cells were stained with anti-CD90.2-BV510, CD4-BV785, CD8-BV711, CD11a-APC, CD49d-APC/Fire750, KLRG1-BV605, and CD62L-BV570 (all BioLegend, San Diego, Calif.) in a mixture of FACS Buffer and Brilliant Stain Buffer (BD Biosciences, Franklin Lakes, N.J.) for 30 minutes at RT per the manufacturer's instructions. Cells were then washed and fixed by incubating in 200 ml 2% PFA for 20 minutes at room temperature, and subsequently permeabilized by incubating for 7 minutes in 0.3% Triton X-100. For intracellular staining, cells were incubated in 100 μL of a cocktail of anti-IFN-γ-PE, TNF-βV570, and IL-2-PerCP/Cy5.5 (BioLegend, San Diego, Calif.) for 30 minutes at 4 C. Following staining, cells were washed and passed through a 40 μm cell strainer prior to analysis on a 5-laser Cytek Aurora flow cytometer. 50,000 live CD90.2$^+$ cells were collected per sample, and data analysis was carried out using FlowJo (BD Biosciences, Franklin Lakes, N.J.).

Statistical Analysis

Analyses were performed using GraphPad Prism version 8.2.1 software (GraphPad Software Inc. San Diego, Calif.). A P value of 0.05 was considered statistically significant. Survival curves were compared using the Gehan-Breslow-Wilcoxon test; other results were compared using ANOVA or Mixed Effects analyses as indicated.

Results

Dose and Delivery Route Influence HSV Vaccine Immunogenicity

Figure 1B:
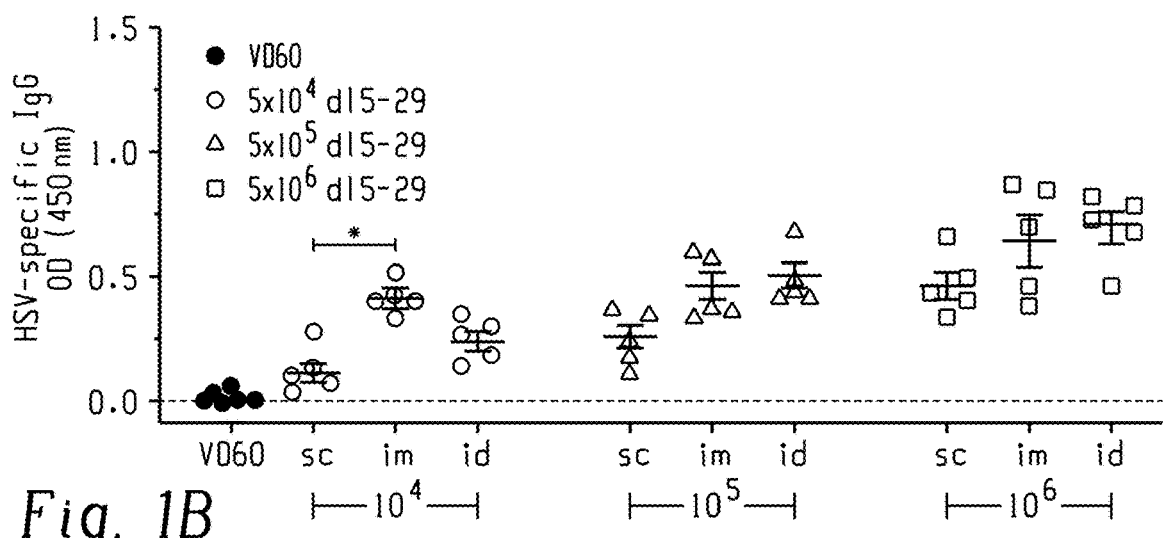
Figure 1C:
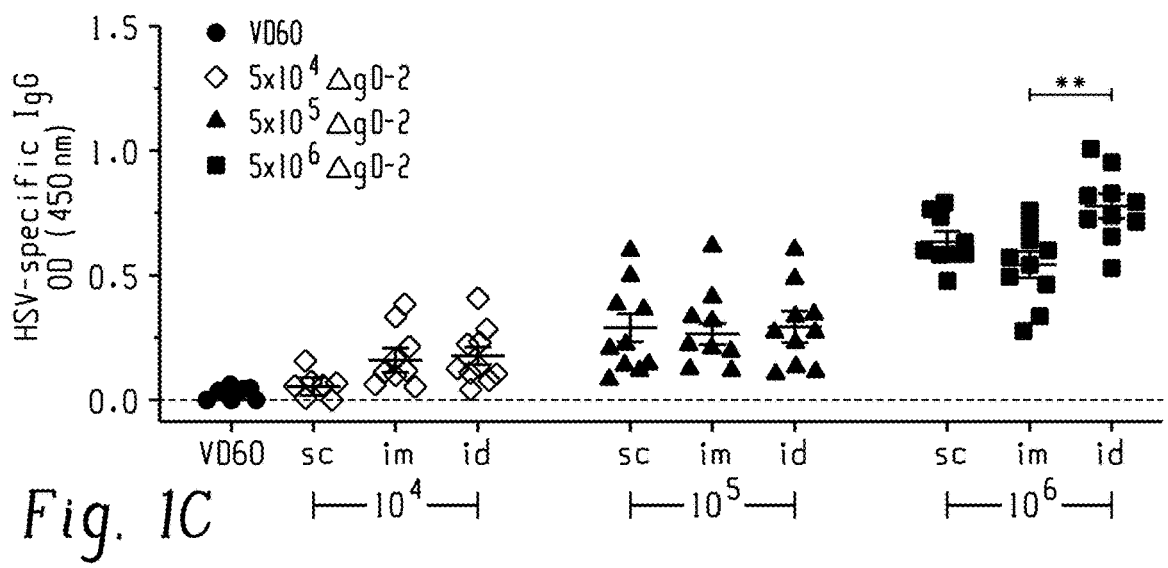

To determine whether the dose and/or route of delivery impacted immunogenicity, mice were prime-boost immunized with increasing doses of ΔgD-2 or dl5-29 ($5\times10^4$, $5\times10^5$ or $5\times10^6$ pfu/dose based on titer on complementing cell lines) or with 5 μg of gD protein adjuvanted with alum and MPL via the sc, im or id route. The total HSV-specific (ELISA), neutralizing and ADCC response (measured using murine FcγRIV activation as a surrogate) were quantified in serum obtained one-week post-boost. The adjuvanted gD protein vaccine elicited a significantly higher total HSV ELISA antibody response when delivered id compared to im or sc ($p<0.001$). The total HSV-specific Ab response to dl5-29 and ΔgD-2 increased with escalation of the dose, but there were few differences comparing route of administration at each dose; the im route induced a significantly higher response compared to sc for dl5-29 at a dose of $5\times10^4$ pfu/mouse ($p<0.05$) and the id route induced a higher Ab response compared to im for ΔgD-2 at a dose of $5\times10^6$ pfu/mouse ($p<0.01$, ANOVA) (FIGS. 1A-C)

Figure 1D:
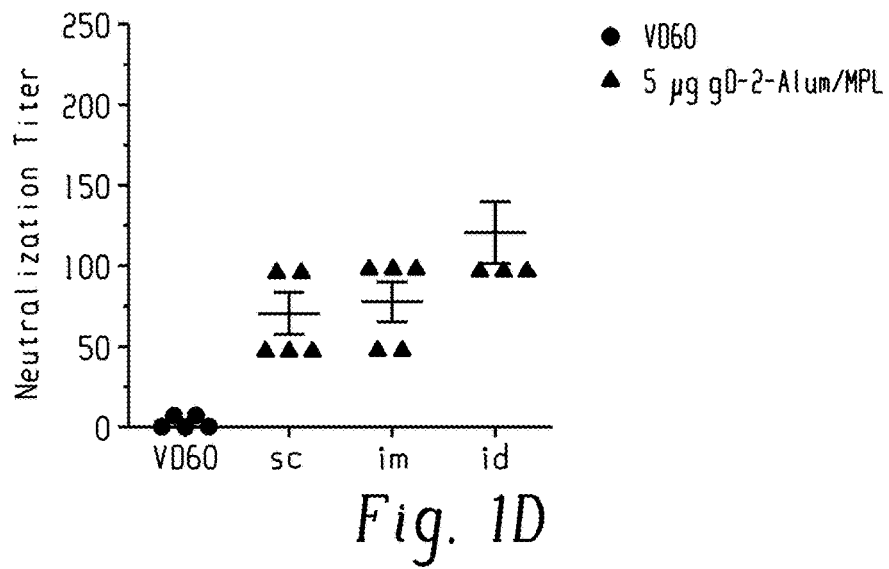
Figure 1E:
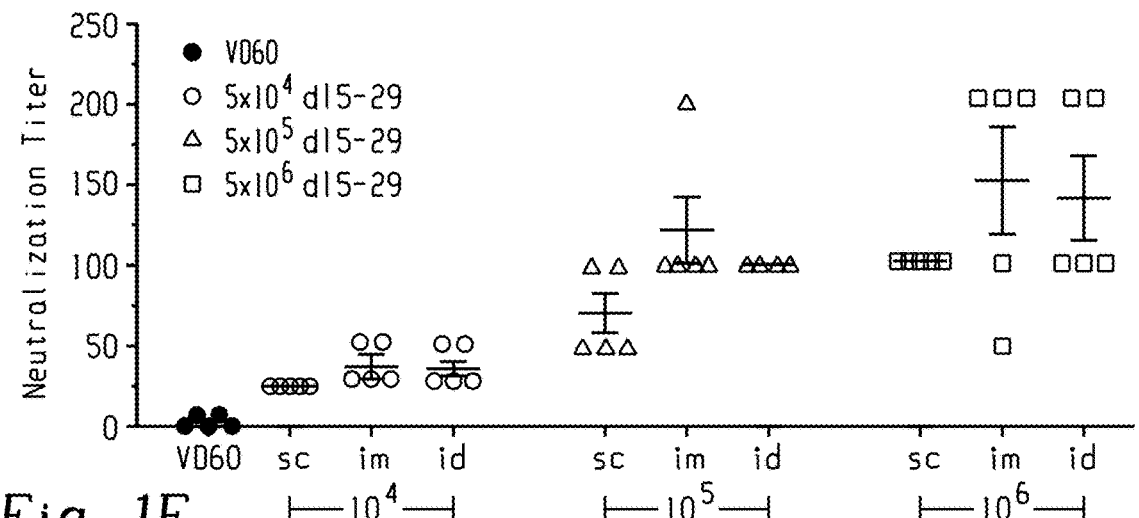
Figure 1F:
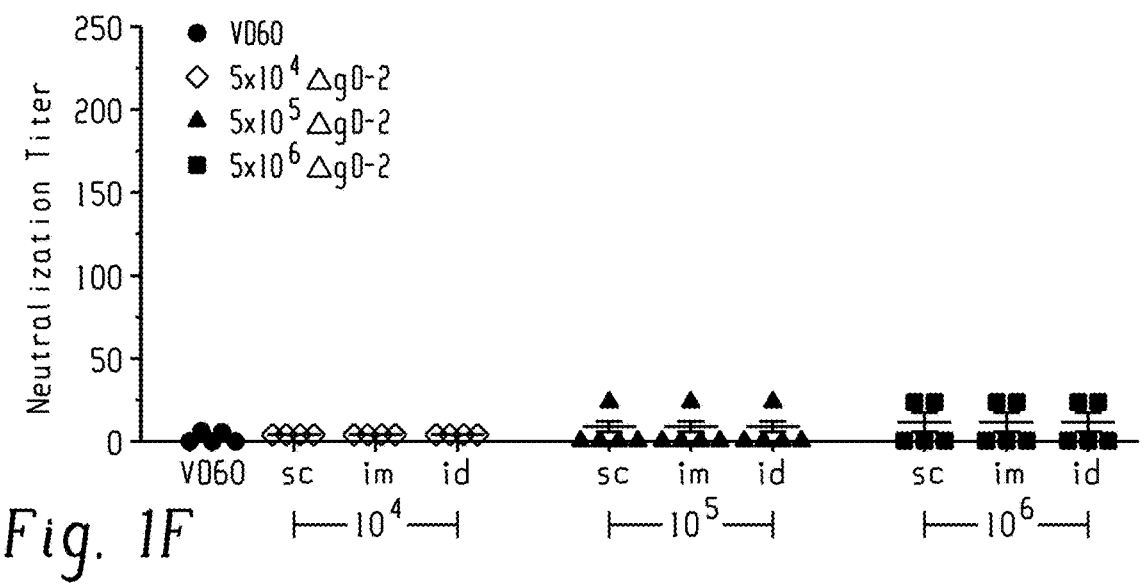
Figure 1G:
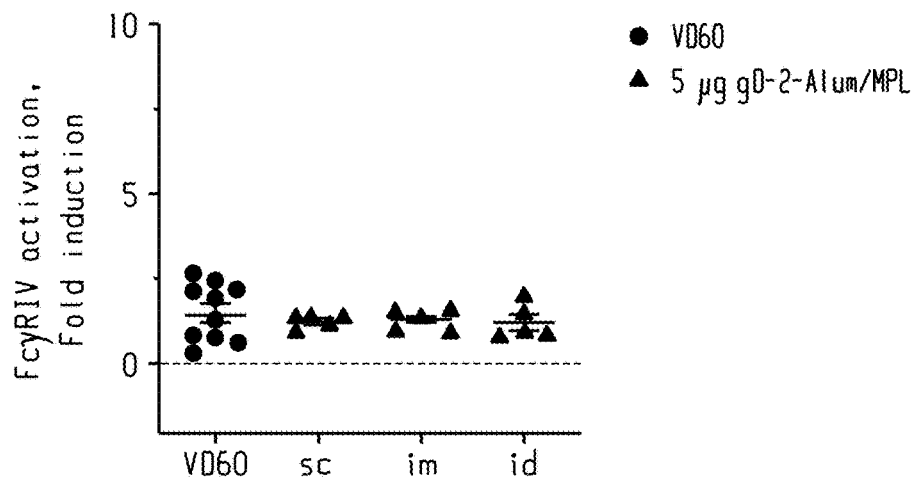
Figure 1H:
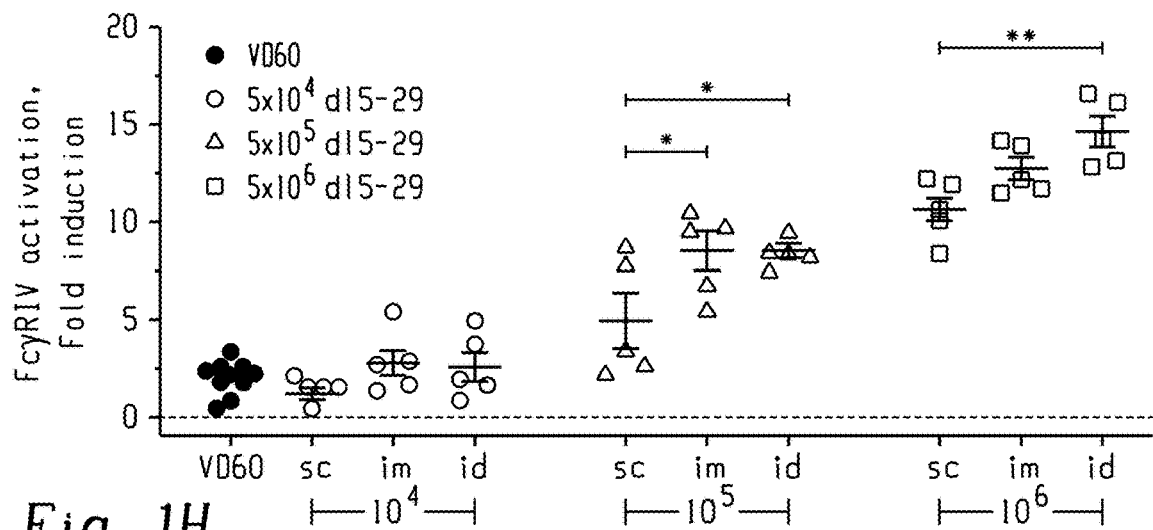
Figure 1I:
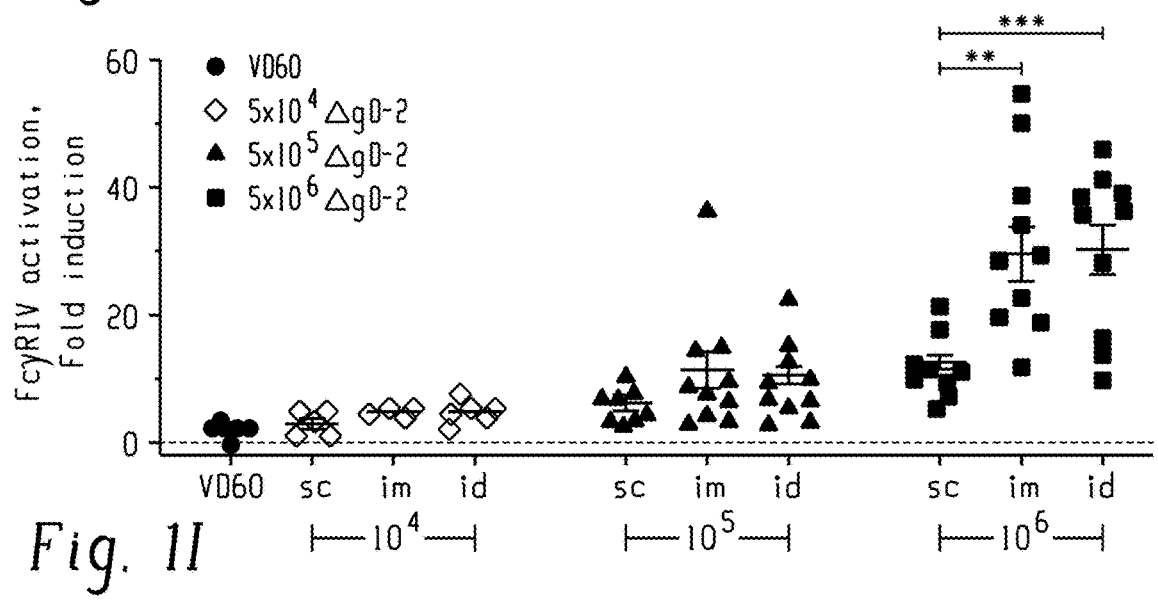

Consistent with the increase in total HSV-specific Abs, there was a nonsignificant increase in the neutralizing titer following id administration of rgD-2/Alum-MPL (FIGS. 1D-F). The neutralizing response to dl5-29 increased with dose, but not when comparing the route of administration. ΔgD-2, as anticipated from prior studies, induced little or no neutralizing Ab response regardless of dose or route of administration. In contrast, ΔgD-2 elicited the most potent ADCC response compared to the other vaccines, which increased with dose and was significantly greater at the $5\times10^6$ dose when comparing id or im to sc administration. The adjuvanted gD protein vaccine induced no ADCC response relative to control serum regardless of route of administration. The dl5-29 vaccine induced an intermediate ADCC response, which was highest following id administration of $5\times10^6$ pfu (median 15-fold) compared to the 30-fold FcγRIV activation elicited by $5\times10^6$ pfu of ΔgD-2 administered im or id. (FIGS. 1G-I).

Figure 2A:
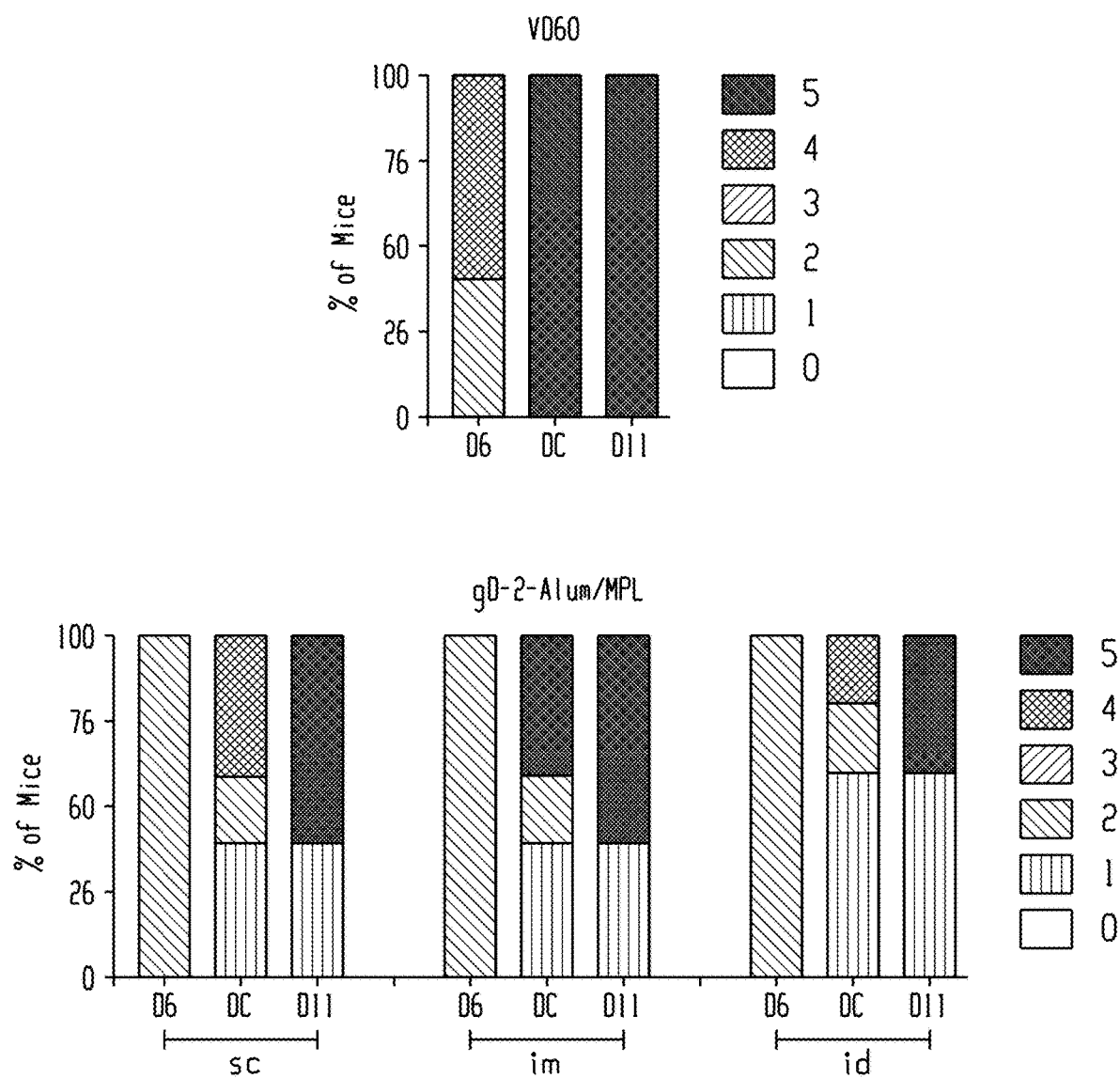
FIGS. 2A-2J. Differences in immunogenicity based on vaccine dose and route translate to differences in protection. Female C57BL/6 mice were vaccinated twice, three weeks apart with $5 \times 10^4$, $5 \times 10^5$ or $5 \times 10^6$ pfu/mouse of dl5-29 or ΔgD-2 or 5 μg gD-2-Alum/MPL subcutaneously (sc), intramuscularly (im) or intradermally (id). Three weeks following the second vaccination, mice were challenged on the skin with 10×LD90 HSV-2 SD90. Disease scores over time are shown for gD-2-Alum/MPL (FIG. 2A), dl5-29 (FIG. 2B) and ΔgD-2 (FIG. 2C). Percentage survival is shown in FIGS. 2D-2J. N=5 mice per group for gD-2-Alum/MPL and dl5-29 in a single experiment; n=5 mice per group, two independent experiments for ΔgD-2. For survival curves, **p<0.01 by Gehan Breslow Wilcoxon test.
Figure 2B:
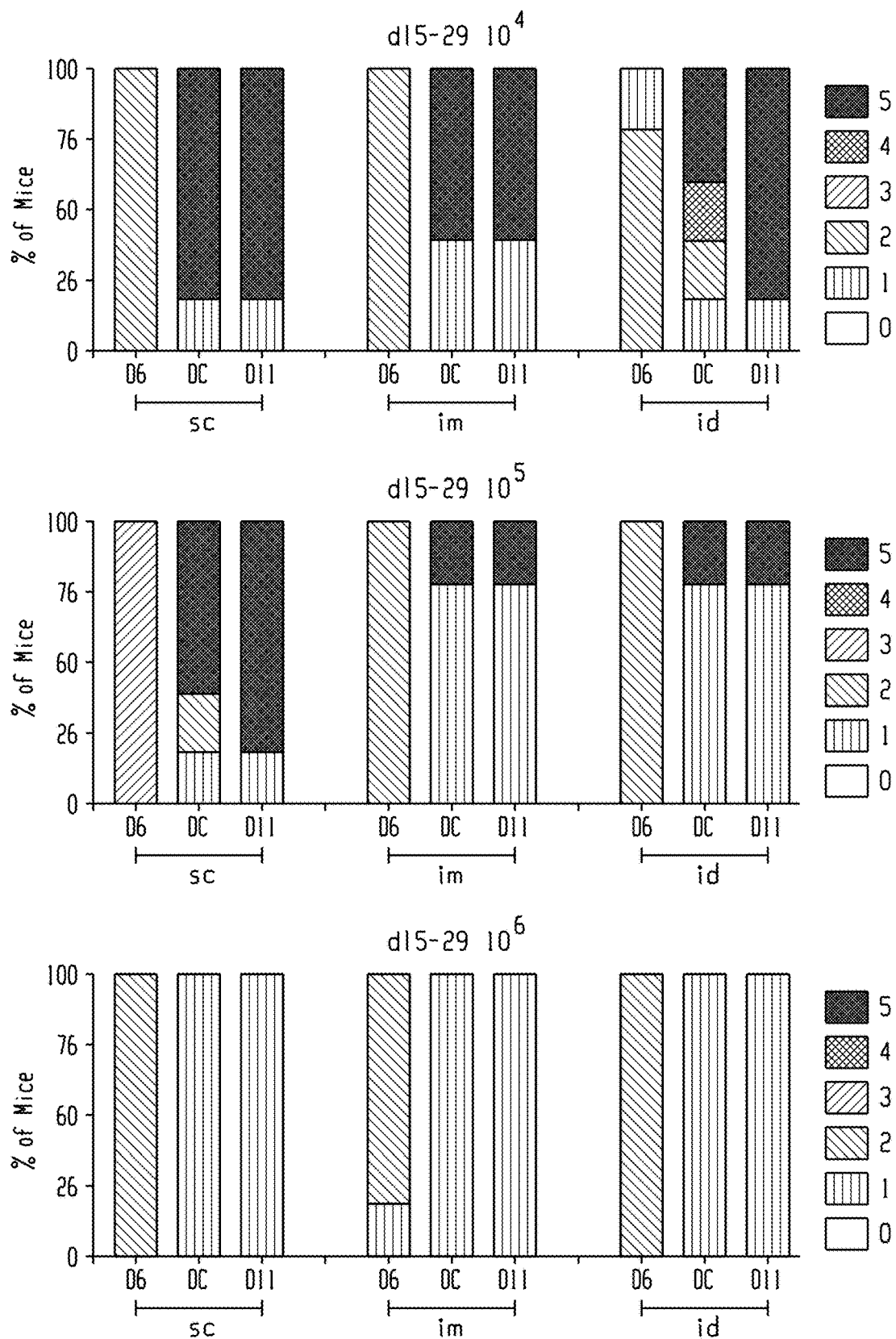
Figure 2C:
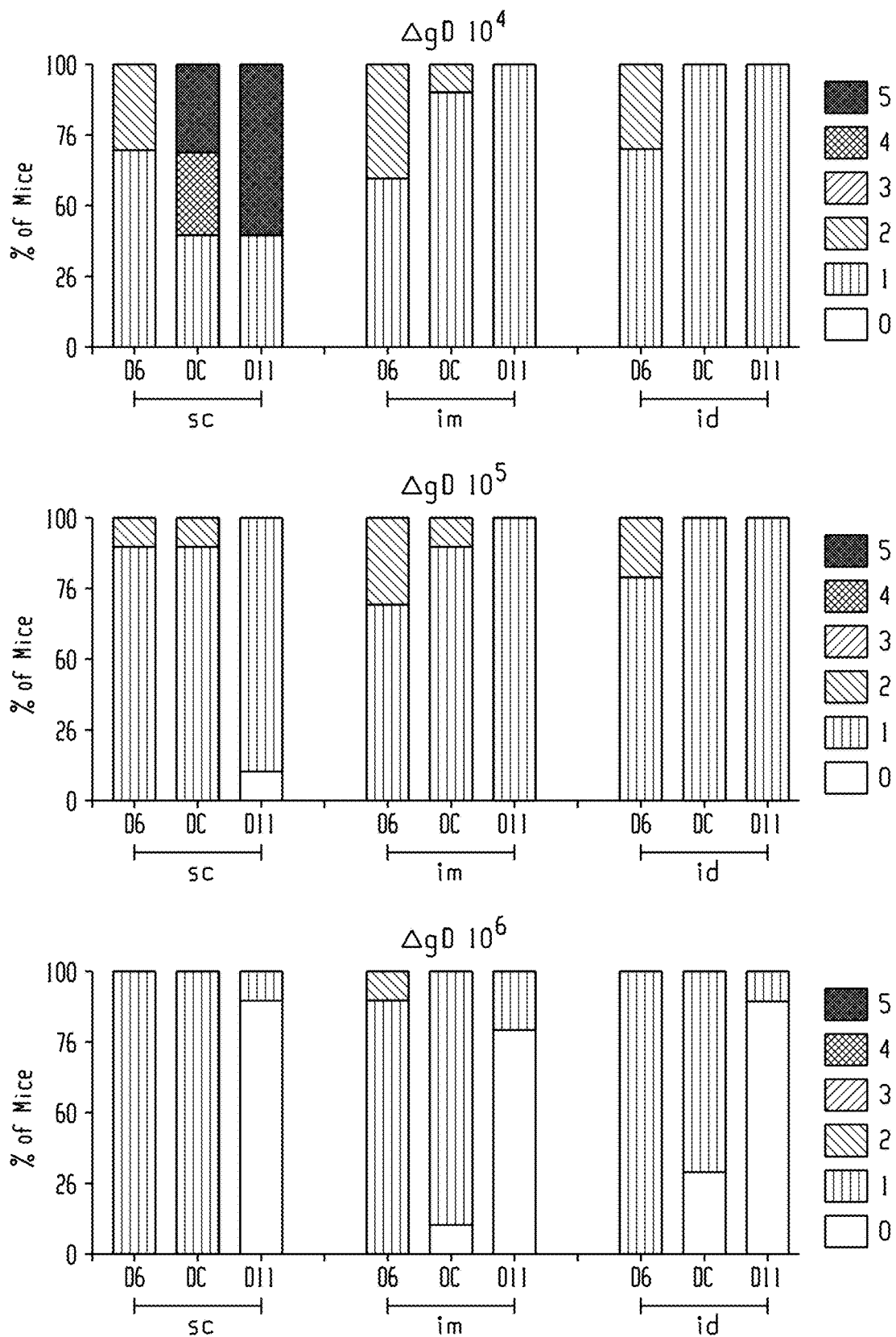
Figure 2D:
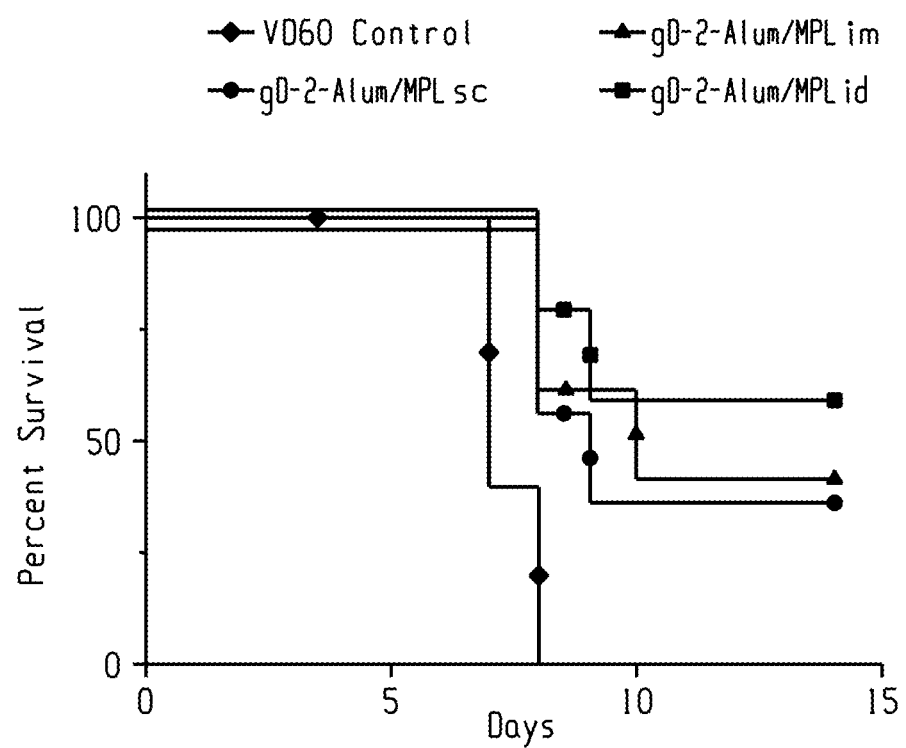
Figure 2E:
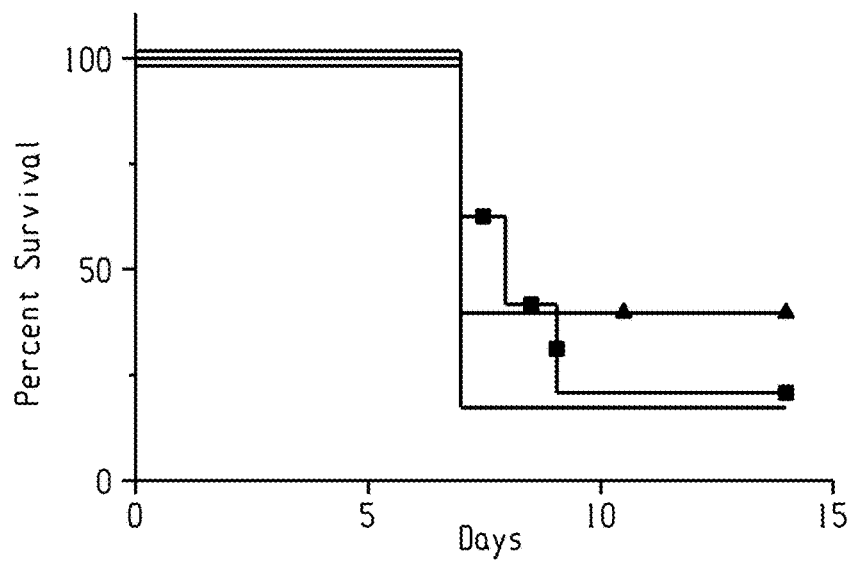
Figure 2F:
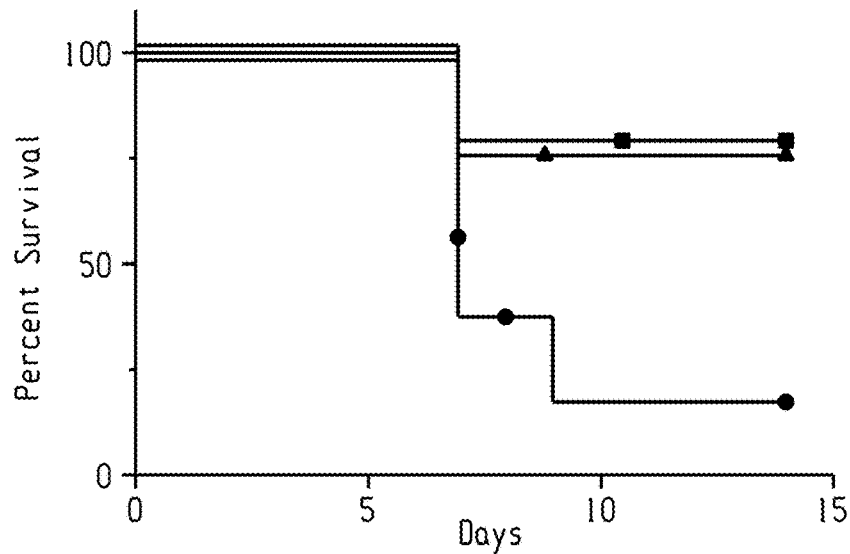
Figure 2G:
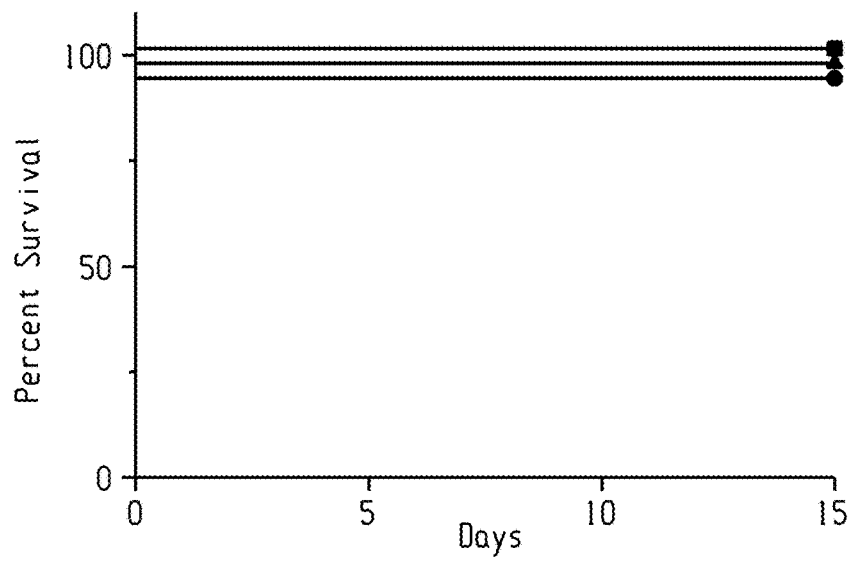
Figure 2H:
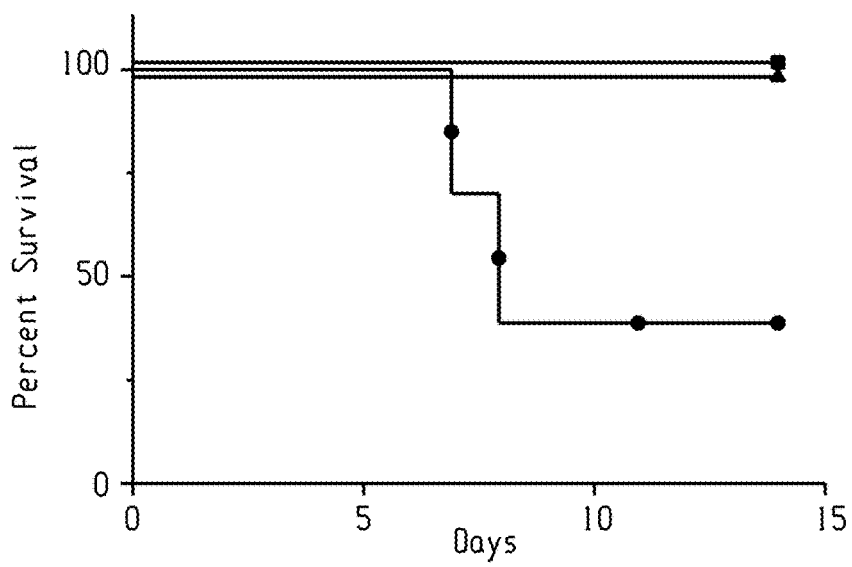
Figure 2I:
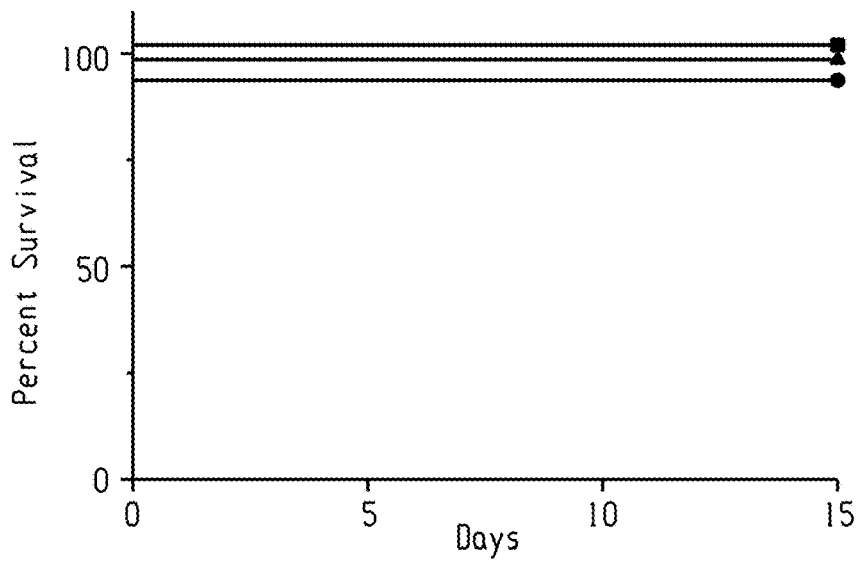
Figure 2J:
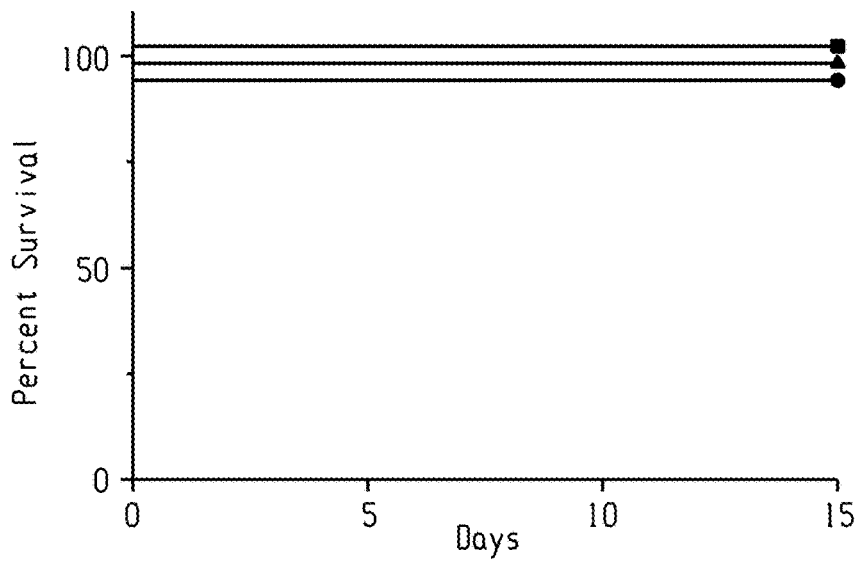

Differences in Immunogenicity Translate to Differences in Protection Following Lethal Skin Challenge The prime-boost vaccinated mice were challenged on the skin with a 10×LD90 dose of the clinical isolate of HSV-2, SD90, which has been previously shown to be consistently lethal in murine models (Dudek, T. E., et al., *Journal of Infectious Diseases* 2011, 203, 1434-1441). Mice were monitored for two weeks for signs of disease and were euthanized if signs of severe skin or neurologic disease were observed as previously described (FIGS. 2A-J) (Petro, C., et al, *eLife* 2015; Petro, C. D., et al, *JCI Insight* 2016, 1, 1-15; Burn, C., et al., *Journal of Infectious Diseases* 2017, 1-5). There was a modest but not significant increase in protection afforded by the adjuvanted protein vaccine when administered id compared to im or sc (FIGS. 2A-C), which parallels the increased ELISA and nAb responses (FIGS. 1A, 1D). Route of administration had no significant impact on survival following $5\times10^4$ dose of dl5-29 (FIG. 2E), which was not protective, but both the im and id routes provided greater protection than sc route following $5\times10^5$ dose of dl5-29 (80% versus 20%)(FIG. 2F), which paralleled the significant increase in ADCC (FIG. 1H). All three routes were fully protective at the highest vaccine dose (FIG. 2G). The only breakthrough in survival with ΔgD-2 was observed with a dose of $5\times10^4$ administered sc (FIG. 2H). Complete protection against lethality was observed at all other doses and routes (FIGS. 2I-J). When examining the association between ADCC and survival across the total population independent of dose, route or vaccine (n=145), 93/96 mice with a 4.5-fold increase in mFcγRIV activation survived compared to 14/49 with <4.5-fold increase ($p<0.0001$, chi-square).

Figure 3A:
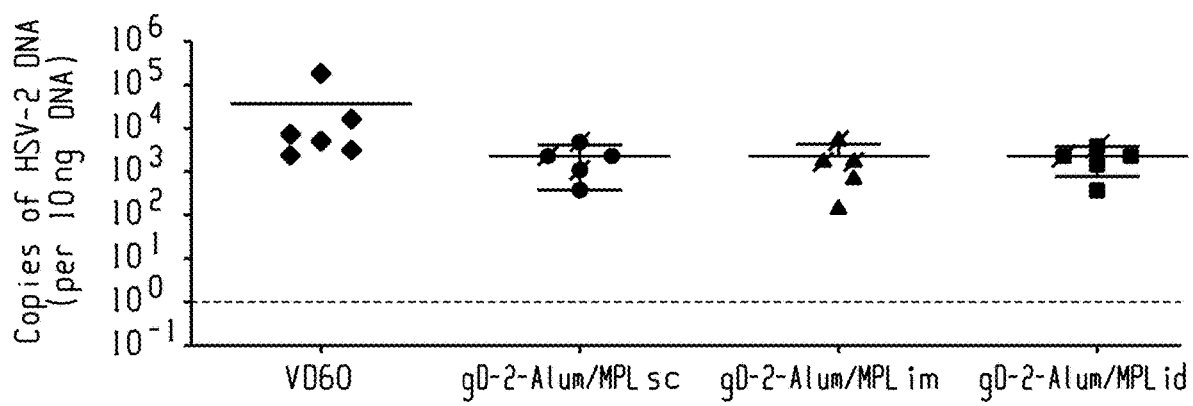
FIGS. 3A-3C. HSV DNA detection in the sacral nerve parallels survival data. Female C57BL/6 mice vaccinated with 5 μg rgD-2-Alum/MPL, or $5 \times 10^5$ pfu/mouse of dl5-29 or ΔgD-2 by the sc, im or id routes were challenged in the skin with 10×LD90 HSV-2 SD90. Following challenge, mice were monitored daily for fourteen days and sacral nerve tissue was harvested at the time of death for mice that succumbed to challenge, or at D14 post challenge for surviving animals. HSV DNA in the sacral ganglia was assessed by qPCR and the number of copies of HSV-2 DNA per 10 ng of DNA is shown in (FIG. 3A) for rgD-2-Alum/MPL, (FIG. 3B) dl5-29 and (FIG. 3C) ΔgD-2. Mice that succumbed to challenge are indicated by a crossed through symbol. There were no significant differences based on vaccine route (ANOVA).
Figure 3B:
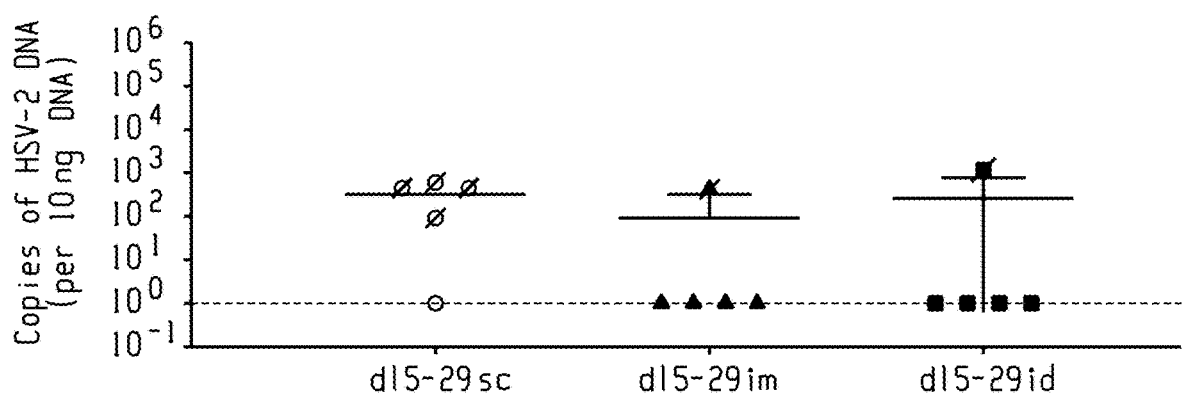
Figure 3C:
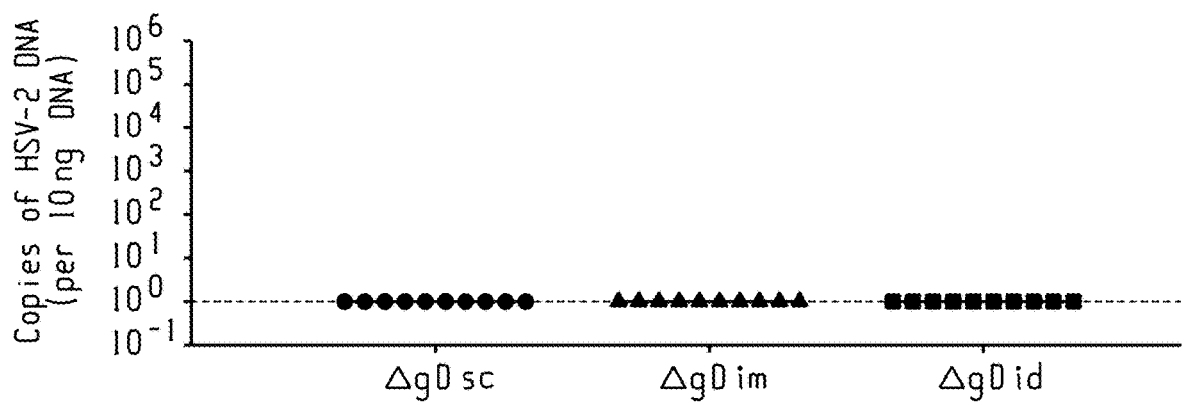

To assess whether the route of vaccination impacted the ability of vaccines to prevent the establishment of latency, HSV viral DNA was quantified in ganglia at the time of death or on day 14 post-challenge. Despite the increase in Ab response following id vaccination with adjuvanted gD protein, there was no reduction in viral DNA recovered from ganglia following any route of immunization. The results with dl5-29 and ΔgD-2 at the $5\times10^5$ dose paralleled the disease scores and survival data. Only 1/5 mice immunized im or id compared to 4/5 mice immunized sc with dl5-29 had HSV DNA detected in the ganglia. No viral DNA was recovered in mice vaccinated by any route with the same dose of ΔgD-2 (FIGS. 3A-C).

ΔgD-2 Vaccination Induces Robust CD4 and CD8 T Cell Memory Responses

Figure 4A:
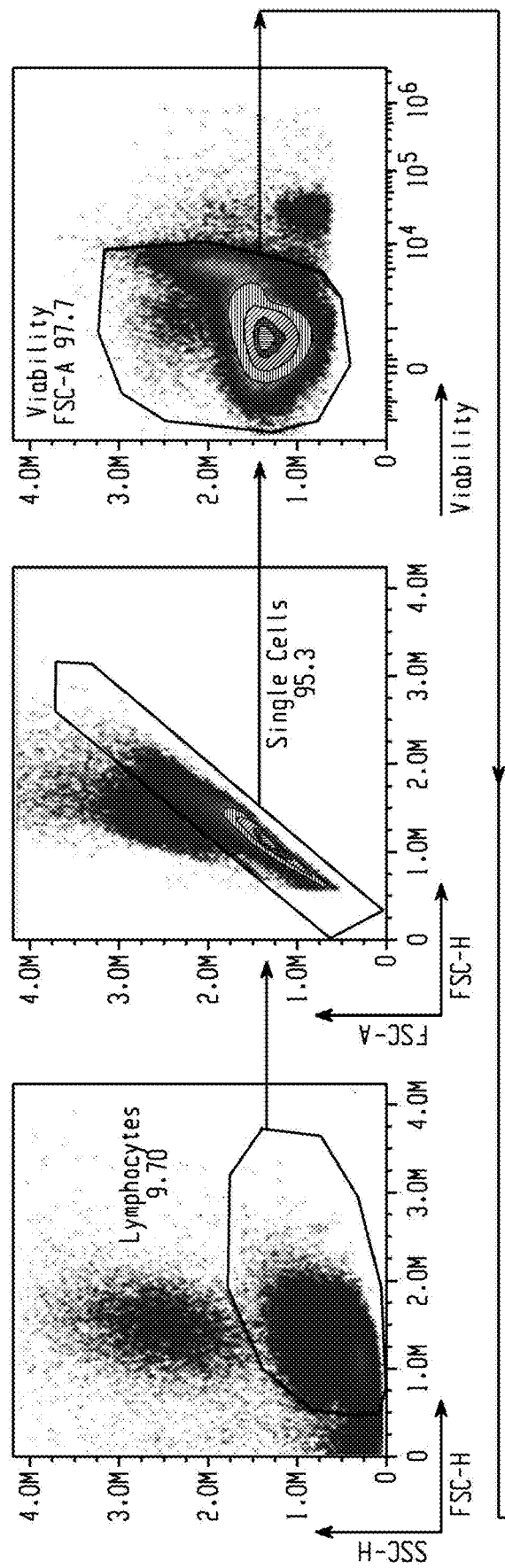
FIGS. 4A-4D. Kinetics of the T cell response following HSV vaccination. Female C57BL/6 mice were vaccinated i.m. twice, three weeks apart, with $5 \times 10^5$ pfu/mouse of ΔgD-2 or 5 μg gD-2-alum/MPL. Before vaccination (day-1) and at week 1 and 2 following prime and boost, mice were retro-orbitally bled and assessed for CD11a$^+$ CD49d$^+$ activated CD4 and CD8 T cells.
Figure 4B:
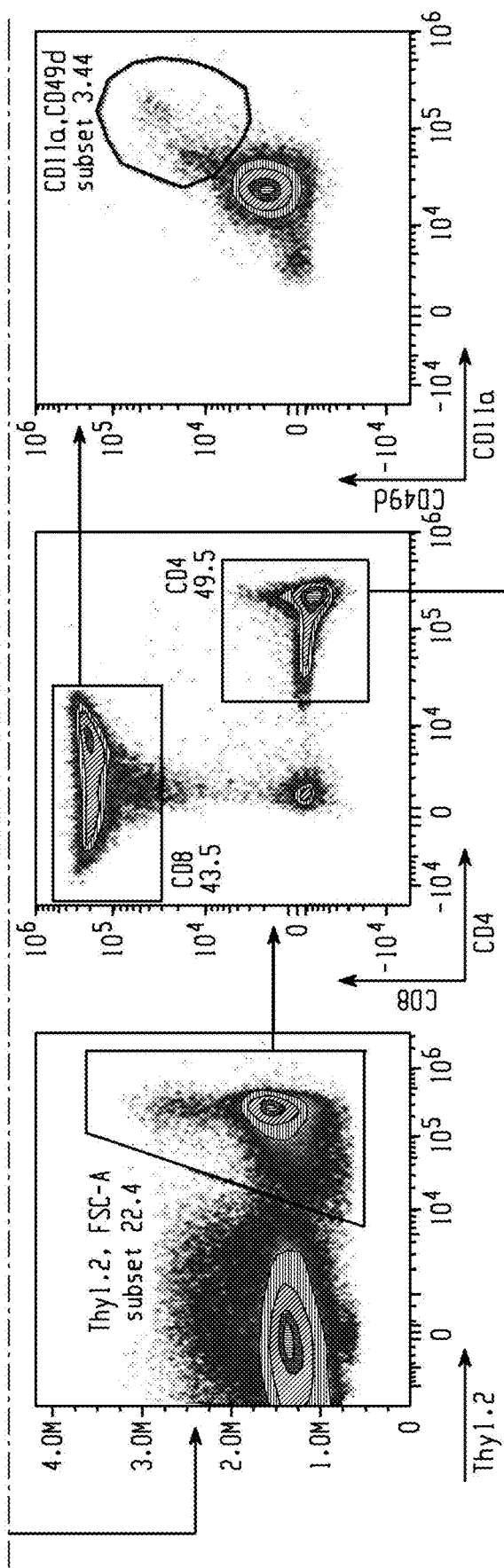
Figure 4B:
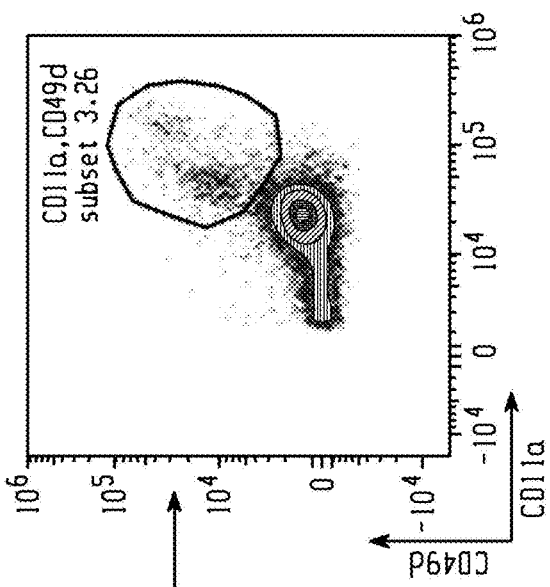
Figure 4C:
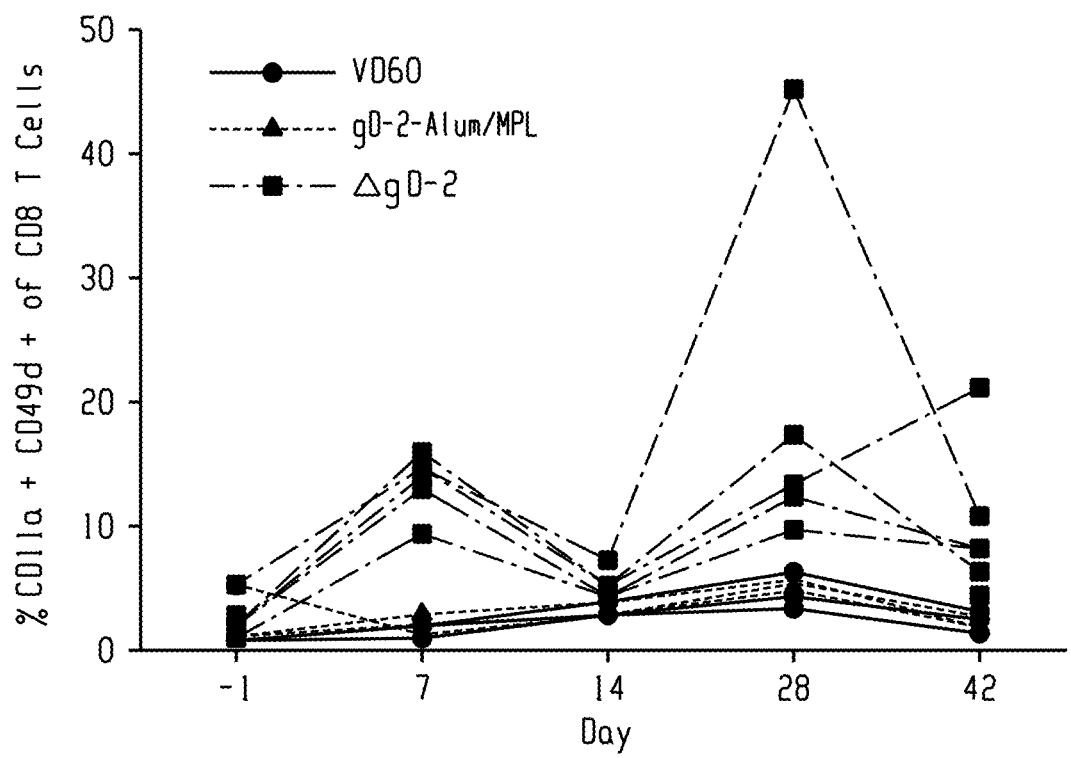
Figure 4D:
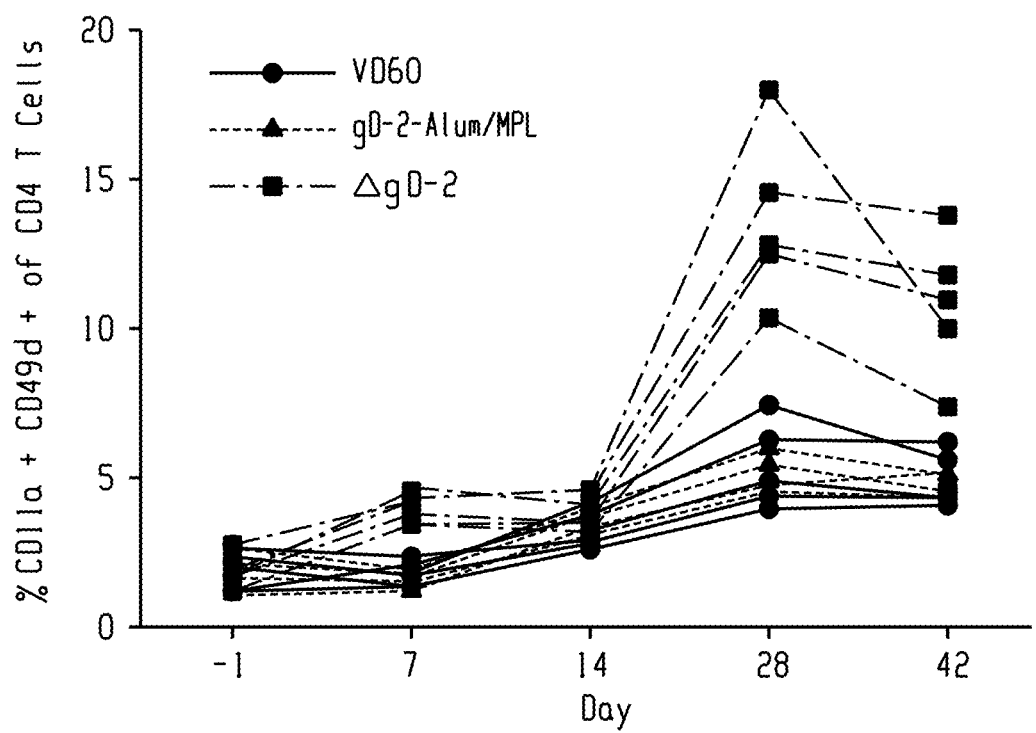
Figure 5A:
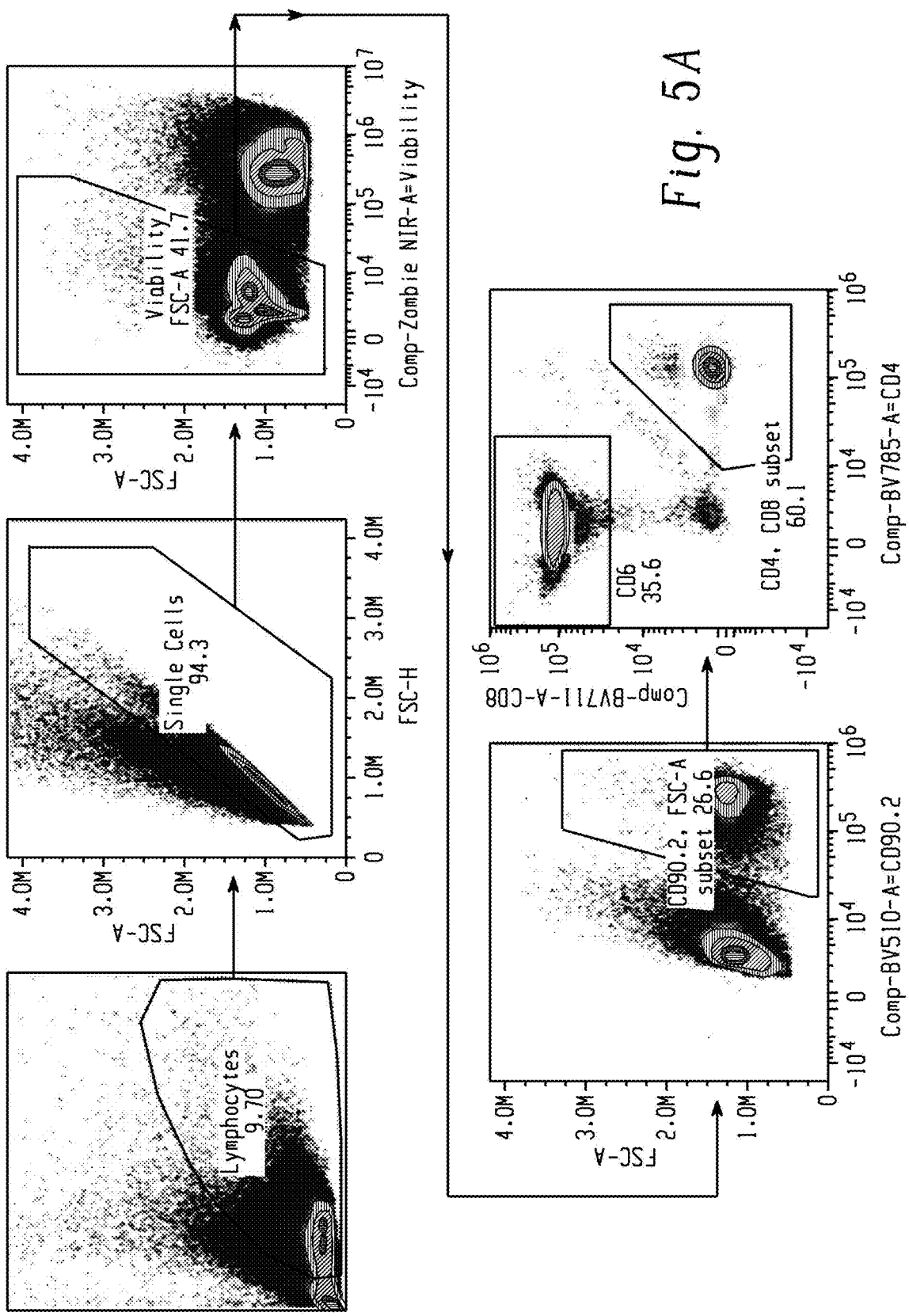
FIGS. 5A-5G. ΔgD-2 vaccination induces polyfunctional CD4 and CD8 T cells that produce IFN-γ, TNF and IL-2 in response to HSV-2 stimulation. Female C57BL/6 mice were vaccinated i.m twice, three weeks apart, with $5 \times 10^5$ pfu/mouse of ΔgD-2 and 5 μg gD-2-alum/MPL. Splenocytes from vaccinated mice were collected two weeks following boost vaccination and stimulated with PHA or UV-inactivated HSV-2 SD90 for 18 hours with Brefeldin A treatment before staining and flow cytometric analysis for the production of IFN-γ, TNF and IL-2. Gating strategy is shown in (FIG. 5A), and cytokine responses for CD4 (FIGS. 5B-D) and CD8 (FIGS. 5E-G) T cells. Data was analyzed by Mixed Effects Analysis, *p<0.5, p<0.01, *p<0.001; n=5 mice per group.
Figure 5B:
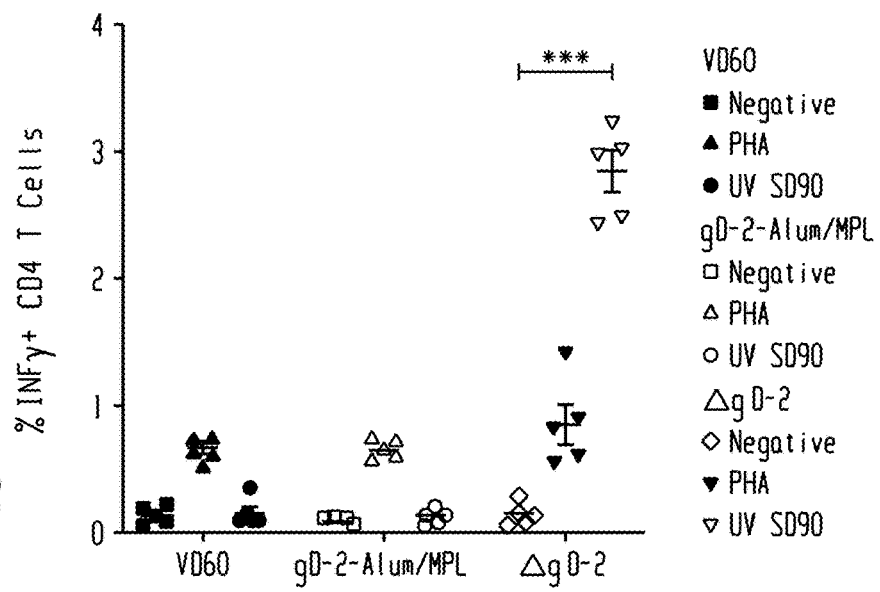
Figure 5C:
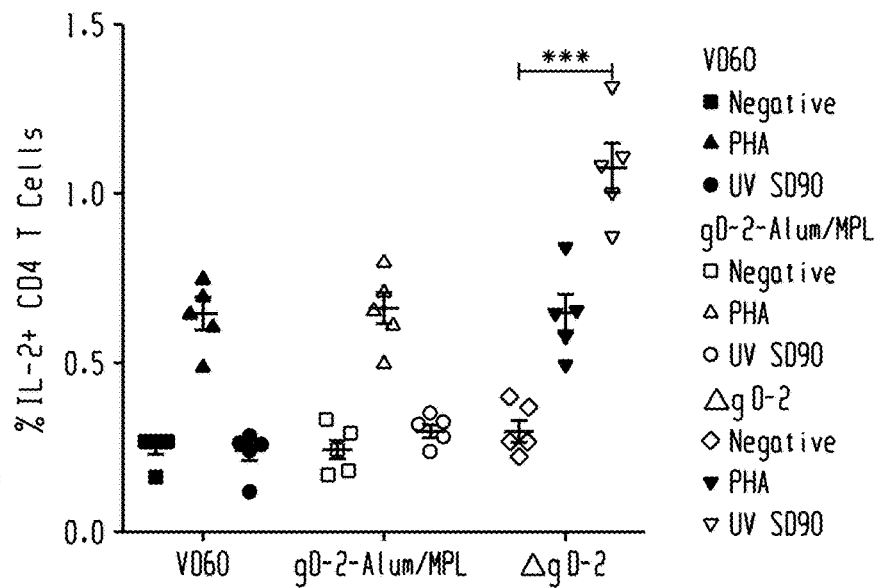
Figure 5D:
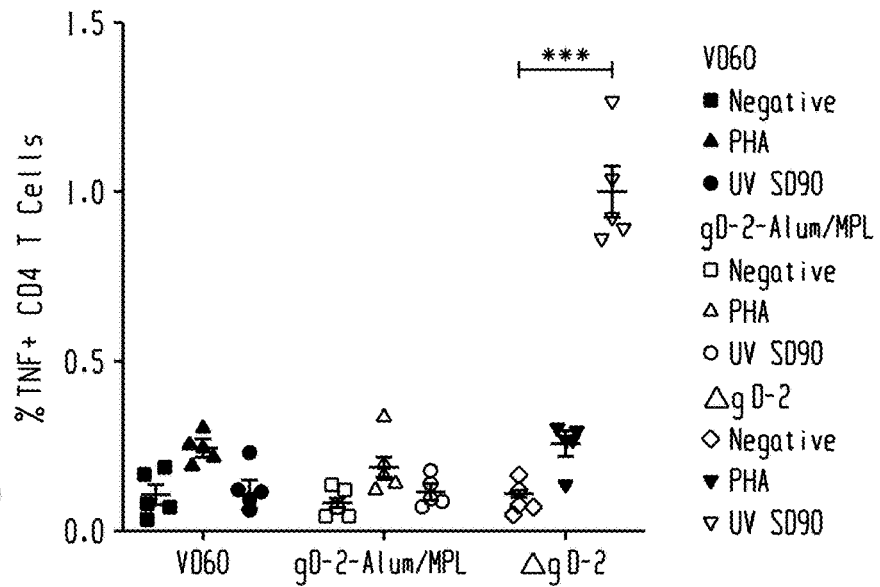
Figure 5E:
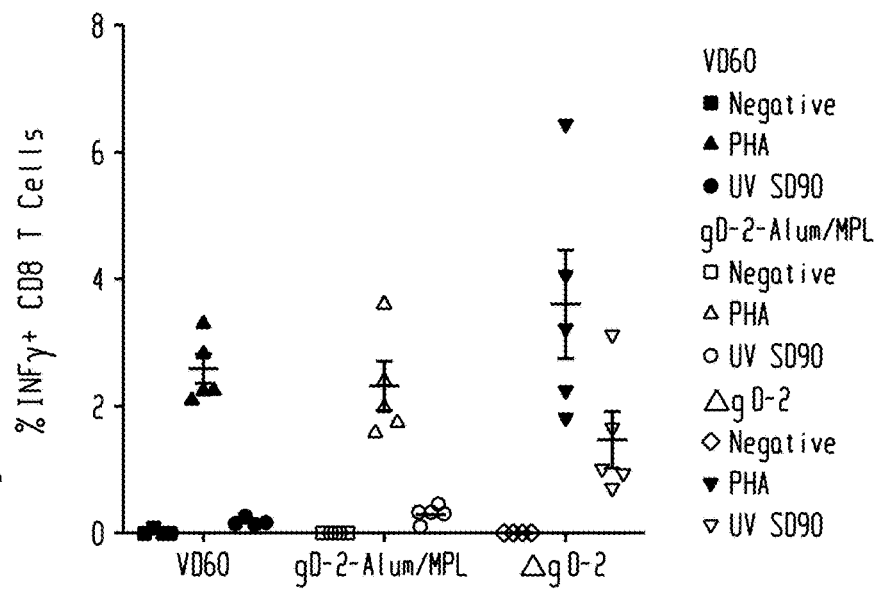
Figure 5F:
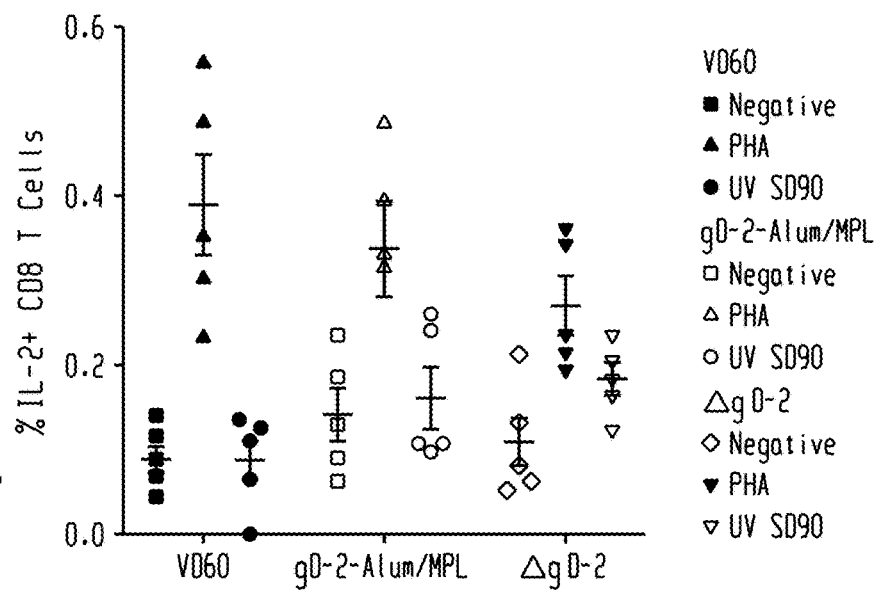
Figure 5G:
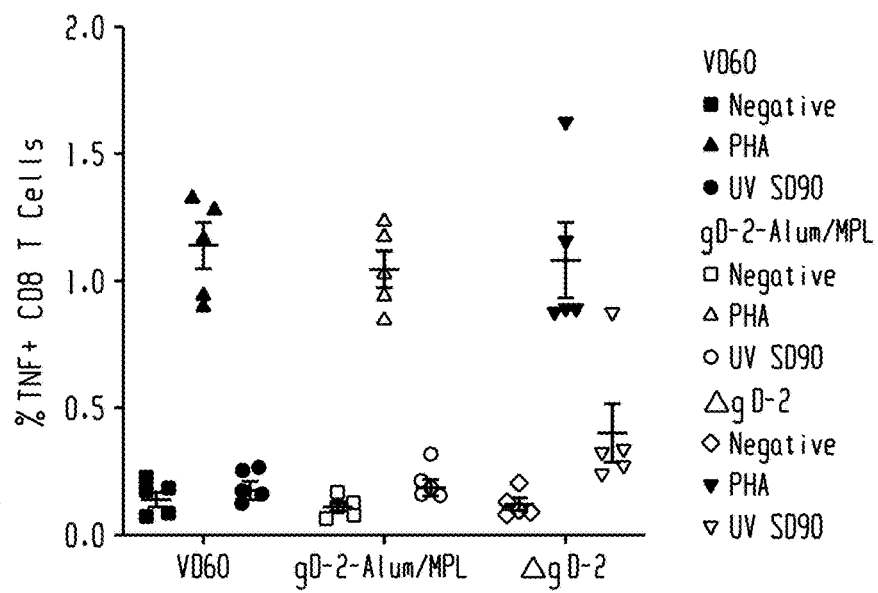

To further phenotype the immune response to ΔgD-2 and rgD-2/Alum-MPL which trigger functionally distinct Ab responses, mice were prime-boost vaccinated i.m with $5\times10^5$ pfu/mouse of ΔgD-2 or 5 μg gD-2-alum/MPL at three week intervals and T cell responses were assessed in the peripheral blood prior to vaccination (Day −1) and at the indicated times post prime and boost. ΔgD-2 induced activated CD4 and CD8 T cells following both prime and boost vaccination as measured by quantifying CD11a+CD49+ CD4 and CD8 T cells. In contrast, there was little detectable T cell response to the adjuvanted protein vaccine (FIGS. 4C-D). The splenocytes from these mice were harvested on Day 42 and stimulated with UV-inactivated SD90 or phytohemagglutinin (PHA) as a viability control to assess cytokine responses. Significantly more IFN-γ, TNF and IL-2 producing CD4+ T cells were observed when splenocytes isolated from ΔgD-2, but not rgD-2/alum-MPL vaccinated mice were stimulated with inactivated virus compared to unstimulated cells (FIGS. 5B-D). The response was greater than observed with the PHA mitogen. There was also a non-significant increase in cytokine-producing CD8 T cell responses to the ΔgD-2 vaccine compared to unstimulated cells (FIGS. 5E-G).

Combination of Low Dose ΔgD-2 with rgD-2 Provides Additive Protection

Figure 6A:
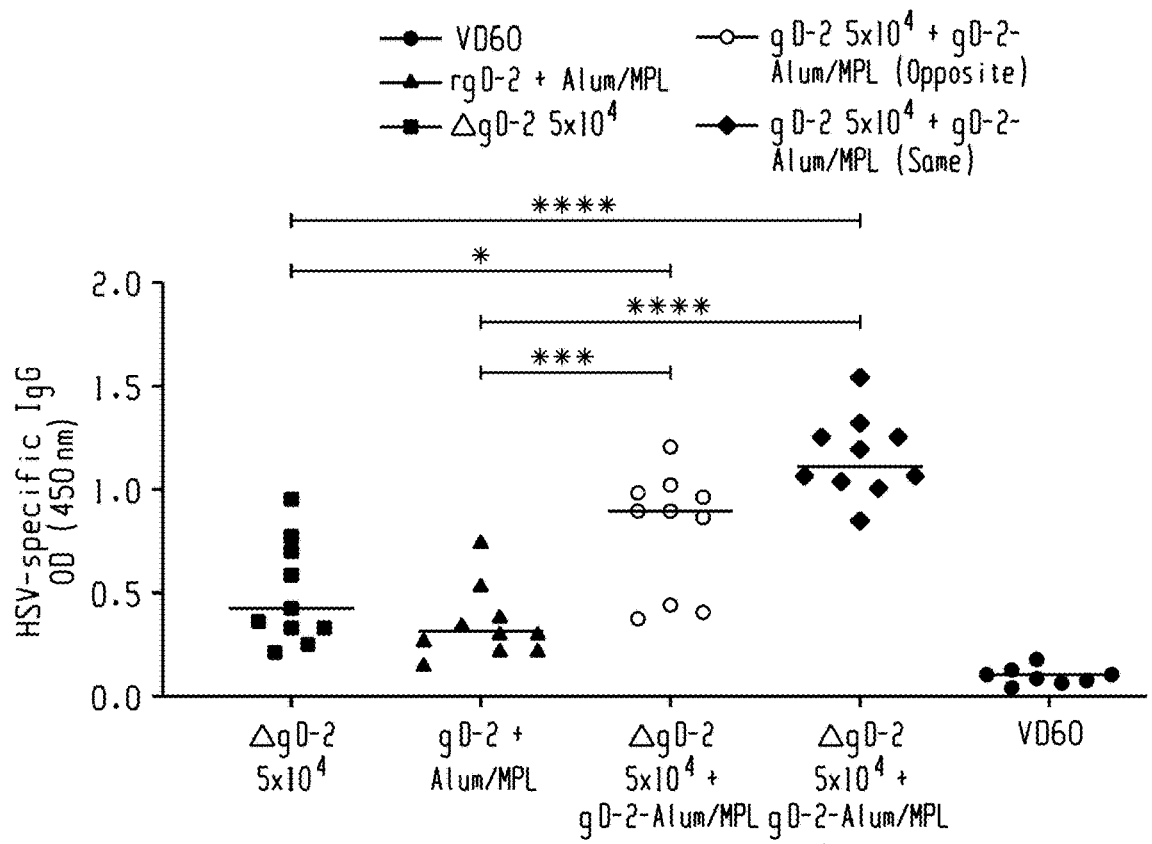
FIGS. 6A-6D. The generation of neutralizing antibody enhances protection by low-dose ΔgD-2. Female C57BL/6 mice were subcutaneously vaccinated twice, three weeks apart with $5 \times 10^4$ pfu/mouse of ΔgD-2, 5 μg gD-2-Alum/MPL or a combination of both vaccines delivered on opposite flanks (opposite) or at the same site (same). One week after the second vaccination, mice were retro-orbitally bled and serum was assessed for total HSV-specific IgG by ELISA (FIG. 6A), neutralizing titer (FIG. 6B), and FcγRIV activation (FIG. 6C). Three weeks after the second vaccination, mice were challenged on the skin with a 10×LD90 dose of HSV-2 (SD90). Percentage survival is shown (FIG. 6D). N=5 mice per group, two independent experiments. (A-C) *p<0.05, p<0.01, *p<0.001, ****p<0.0001 by ANOVA. For survival curves, *p<0.05, ***p<0.001 by Gehan Breslow Wilcoxon test.
Figure 6B:
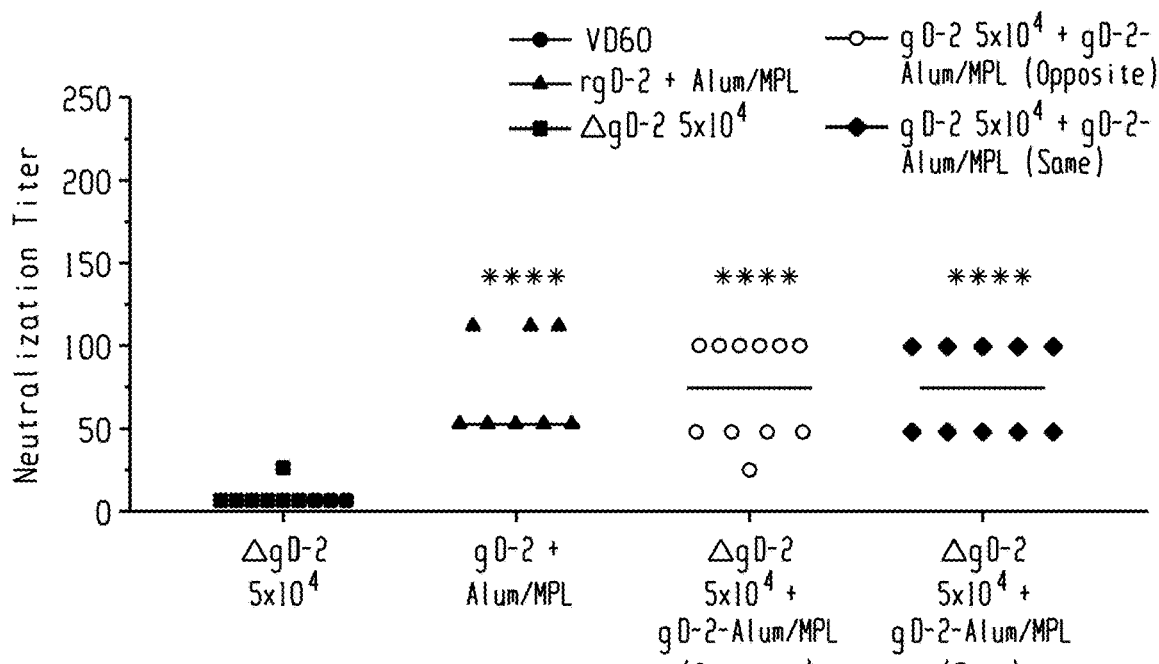
Figure 6C:
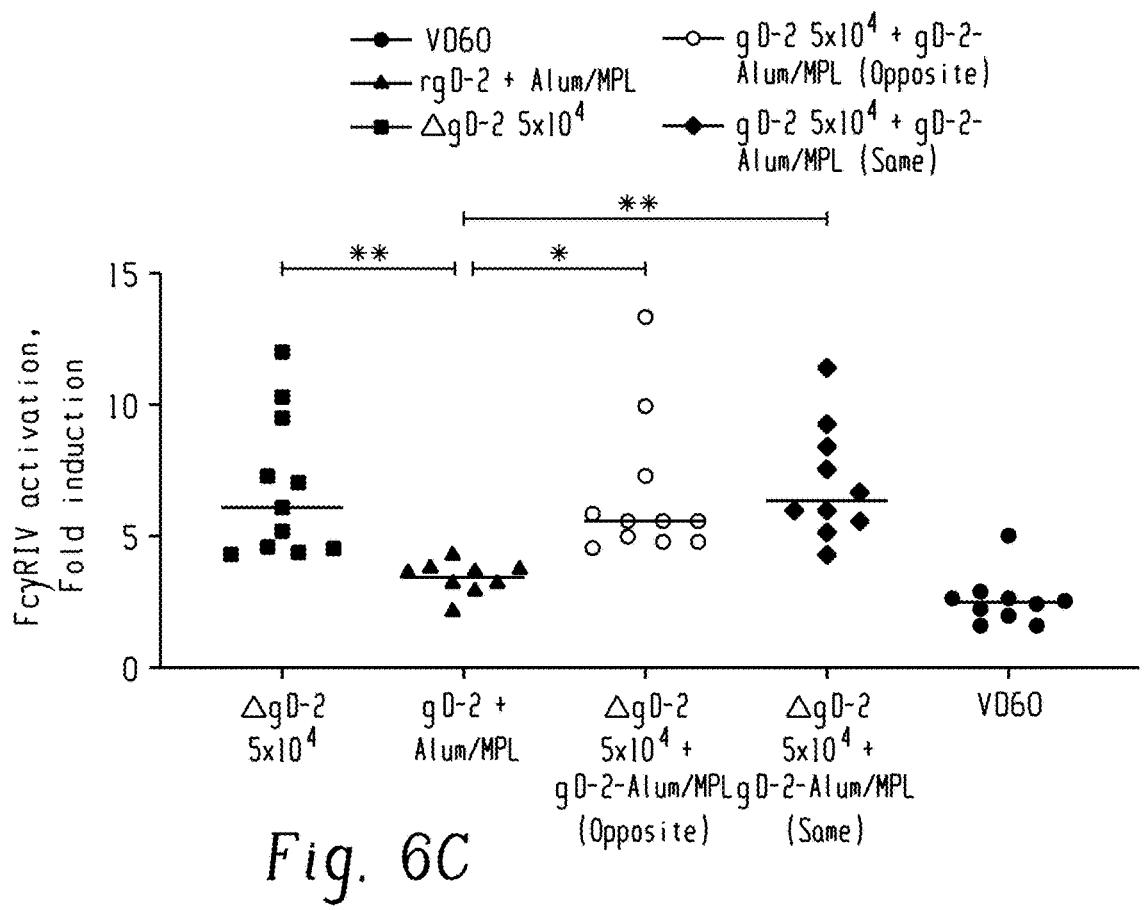
Figure 6D:
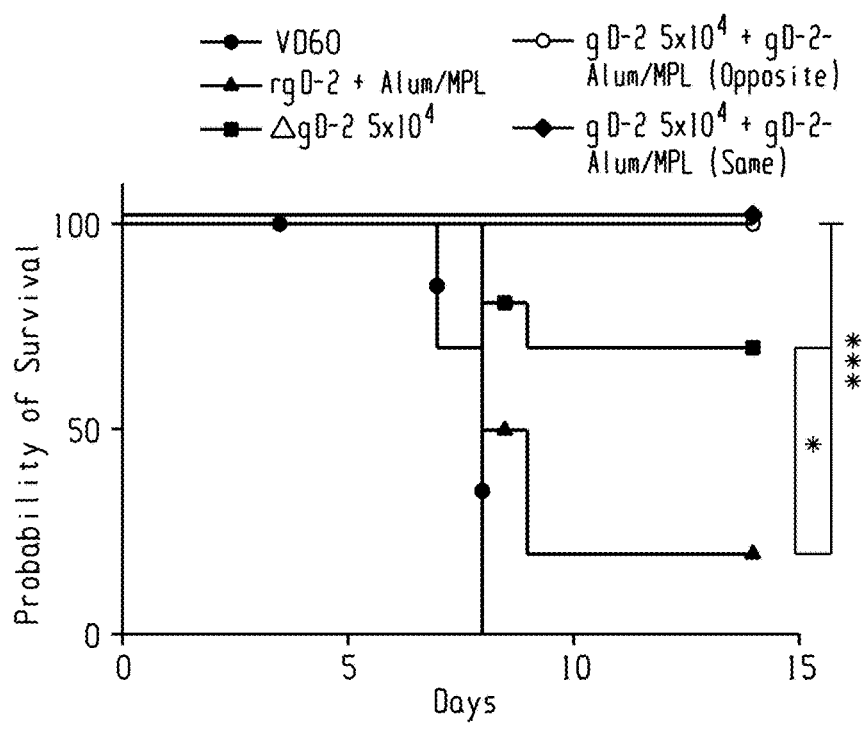

To determine whether the combination of ΔgD-2 and rgD-2/Alum-MPL is beneficial or antagonistic, mice were vaccinated sc with a dose of ΔgD-2 that is not fully protective ($5 \times 10^4$ pfu/mouse), 5 µg of gD-2-Alum/MPL, or a combination of both vaccines delivered on opposite or the same flank. We used the less efficient route of vaccination to accentuate any potential beneficial effects. Both combinations significantly increased the total HSV-specific antibody response compared to either vaccine alone (FIG. 6A). The combinations had no additive or antagonistic effect on the nAb response to rgD-2/Alum-MPL (FIG. 6B) or the ADCC response to ΔgD-2 (FIG. 6C) and resulted in 100% protection against a 10×LD90 skin challenge with HSV-2 (SD90), compared to the 20% and 60% protection observed with administration of rgD-2/Alum-MPL or ΔgD-2, respectively (FIG. 6D). There was no difference when the combination was administered on opposite or the same flank.

Discussion

Clinical studies with HSV vaccine candidates have proven disappointing despite promising preclinical data with vaccines designed to elicit neutralizing antibody responses primarily targeting gD. Preclinical studies with ΔgD-2 have challenged the reliance on neutralizing Abs and have demonstrated that subcutaneous vaccination with $10^5$ (or higher) pfu of ΔgD-2 reproducibly provides complete protection against lethal skin, vaginal or ocular challenge with clinical isolates of HSV-1 or HSV-2 (Petro, C., et al, *eLife* 2015; Petro, C. D., et al, *JCI Insight* 2016, 1, 1-15; Burn, C., et al., *Journal of Infectious Diseases* 2017, 1-5; Ramsey, N. L. M., et al., *J. Virol.* 2020). Protection is mediated by ADCC rather than neutralizing Abs, as evidenced by passive transfer studies. Immune serum from ΔgD-2, but not rgD-2/Alum-MPL vaccinated mice completely protects naïve wild-type, but not FcγRIV knockout mice from lethal challenge (Petro, C., et al, *eLife* 2015; Petro, C. D., et al, *JCI Insight* 2016, 1, 1-15; Burn, C., et al., *Journal of Infectious Diseases* 2017, 1-5; Kao, C. M., et al., *Journal of Infectious Diseases* 2019, 42, 47-10; Burn Aschner, C., et al, *npj Vaccines* 2020, 1-33).

The current studies provide further evidence that ADCC provides a more predictive correlate of immune protection compared to neutralizing responses in mice. The increase in protection observed by increasing the dose and route of delivery of dl5-29 was associated with a significant increase in the ADCC, but not the neutralizing response. Moreover, the only dose and route of vaccination with ΔgD-2 that did not provide 100% protection against a 10×LD90 challenge with SD90, sc immunization with $10^4$ pfu, elicited a mean ADCC response of 2.8-fold (FcγRIV) activation. Only 3 out of 96 mice with a FcγRIV fold increase ≥4.5 succumbed to the high dose lethal challenge regardless of vaccine dose or delivery route.

Both the im and id routes of vaccination induced significantly higher total and/or ADCC responses compared to the sc route. The observation that im and id are more immunogenic than sc is consistent with studies with other vaccines, but a link between route of administration and Ab function (ADCC versus neutralizing) has not been previously described, Improved immunogenicity via the im or id routes could reflect longer antigen retention, differential exposure to antigen presenting cells resident in the dermis and/or greater access to lymphatic drainage (Wahl, M., et al., *Scand. J. Infect. Dis.* 1987, 19, 617-621; Bryan, J. P., et al., *Clin. Infect. Dis.* 1992, 14, 697-707; Rahman, F., et al., *Hepatology* 2000, 31, 521-527; Belshe, R. B., et al, *N Engl J Med* 2004, 351, 2286-2294; Van Damme, P., et al., *Vaccine* 2009, 27, 454-459). For example, intramuscular administration of trivalent inactivated influenza vaccine resulted in higher antibody responses than subcutaneous vaccination in elderly subjects (Gillet, Y., et al, *BMC Med* 2009, 7, 16). However, similar Ab and T cell responses were reported with live attenuated measles, mumps and rubella vaccination delivered sc or im (Laurent, P. E., et al, *Vaccine* 2010, 28, 5850-5856). Despite technical difficulties delivering consistent doses via the intradermal route, intradermal rabies vaccination has been a standard since the World Health Organization recommendation in 1992 because a lower dose achieves comparable immunogenicity (Dubois, B., et al, *Journal of Leukocyte Biology* 1999, 66, 224-230). Intradermal vaccination is presumed to activate a stronger dendritic cell-mediated response thus requiring a lower antigenic dose (Peng, S. L., et al., *Proc. Natl. Acad. Sci. U.S.A.* 2002, 99, 5545-5550). However, we observed no significant difference in ADCC responses or vaccine protection comparing id or im immunization routes at any of the doses for dl5-29 or ΔgD-2, suggesting that the id route does not provide a dose advantage for these vaccines. We did however observe a statistically significant increase in total HSV-specific Ab responses to the subunit vaccine with the id route of administration, which resulted in a nonsignificant increase in neutralizing titer and in vaccine protection.

In addition to dose and delivery route, the vaccine composition also influence immunogenicity as evidenced by the exclusive neutralizing response to the gD subunit vaccine, non-neutralizing, FcγR-mediated response to ΔgD-2, and a combination of both neutralizing and non-neutralizing responses elicited by dl5-29. The absence of any neutralizing Ab following ΔgD-2 immunization likely reflects the absence of the dominant target of nAbs in mice. In other studies, we found that depletion of the gD-specific Ab from dl5-29 immune serum resulted in a significant reduction in neutralizing, but not ADCC titers, indicating that gD is not a target of the ADCC response (Burn Aschner and Herold, mspt. submitted). IgG subclass switching to IgG2, which has the strongest affinity for mFcγRIV and is associated with ADCC in mice, requires interactions within the germinal center between antigen presenting cells, T cells and B cells (Sattentau, Q, et al, *Nat Rev Micro* 2008, 6, 815-826). Consistent with the requirement for T cells in the generation of potent ADCC responses, we documented robust activation of CD4 and CD8 T cells after prime and boost vaccination, while gD-2-alum/MPL elicited little T cell activation. Stimulation of the memory T cells harvested from the ΔgD-2, but not rgD-2/alum-MPL vaccinated mice, with inactivated virus result in IFN-γ, TNF and IL-2 production, which was particularly robust for CD4+ T cells. These differences support the notion that vigorous T cell responses contribute to the generation of ADCC responses.

A combination of adjuvanted rgD-2 and a low dose of ΔgD-2 delivered simultaneously at the same or opposite flank did not interfere with the immunogenicity of either vaccine and was more protective than rgD-2-Alum/MPL alone. This is consistent with our superinfection murine studies, which showed that pre-existing gD neutralizing Abs did not interfere with the immunogenicity of ΔgD-2. Vaccination of HSV-1 seropositive mice with ΔgD-2 boosted the ADCC (but not the neutralizing) Ab response and resulted in complete protection if the mice were subsequently challenge with a lethal dose of HSV-2 (Burn Aschner, C., et al, *npj Vaccines* 2020, 1-33). Thus, while nAbs to gD alone are not sufficient to protect mice (or to date, humans), a combination of both types of responses could be beneficial. Without being limited by theory, one reason for the incomplete protection mediated by nAbs may be the ability of HSV to evade neutralization by spreading directly from cell-to cell. However, it is important to note that delivering recombinant gD protein at the same time as ΔgD-2 is different from having gD present in the viral envelope. In other studies, we found that envelope gD interferes with the generation of IgG2 subclass switched Abs through interactions with herpesvirus entry mediator (HVEM), also known as tumor necrosis factor receptor superfamily member 14 (Burn Aschner and Herold, mspt under review). This likely contributes to the lower levels of ADCC generated by dl5-29 as shown in the current study as well as the low levels generated in response to sublethal infection (Kao, C. M., et al, *Journal of Infectious Diseases* 2019, 42, 47-10; Burn Aschner, C., et al, *npj Vaccines* 2020, 1-33).

Taken together, the current studies provide further evidence that ADCC is an important correlate of immune protection. Although we initially hypothesized that the intradermal route of delivery would prove more immunogenic for all three vaccines, this was only observed with the gD protein subunit vaccine. Both im and id routes provided similar antibody responses and protection with ΔgD-2 and dl5-29. Overall, ΔgD-2 induced the highest ADCC responses and the most potent protection against lethal challenge and latency.

The compositions, methods, and articles can alternatively comprise, consist of, or consist essentially of, any appropriate materials, steps, or components herein disclosed. The compositions, methods, and articles can additionally, or alternatively, be formulated so as to be devoid, or substantially free, of any materials (or species), steps, or components, that are otherwise not necessary to the achievement of the function or objectives of the compositions, methods, and articles.

The terms "first," "second," and the like, do not denote any order, quantity, or importance, but rather are used to distinguish one element from another. The terms "a" and "an" and "the" do not denote a limitation of quantity and are to be construed to cover both the singular and the plural, unless otherwise indicated herein or clearly contradicted by context. "Or" means "and/or" unless clearly stated otherwise. Reference throughout the specification to "some embodiments", "an embodiment", and so forth, means that a particular element described in connection with the embodiment is included in at least one embodiment described herein, and may or may not be present in other embodiments. In addition, it is to be understood that the described elements may be combined in any suitable manner in the various embodiments. A "combination thereof" is open and includes any combination comprising at least one of the listed components or properties optionally together with a like or equivalent component or property not listed Unless specified to the contrary herein, all test standards are the most recent standard in effect as of the filing date of this application, or, if priority is claimed, the filing date of the earliest priority application in which the test standard appears.

Unless defined otherwise, technical and scientific terms used herein have the same meaning as is commonly understood by one of skill in the art to which this application belongs. All cited patents, patent applications, and other references are incorporated herein by reference in their entirety. However, if a term in the present application contradicts or conflicts with a term in the incorporated reference, the term from the present application takes precedence over the conflicting term from the incorporated reference.

While particular embodiments have been described, alternatives, modifications, variations, improvements, and substantial equivalents that are or may be presently unforeseen may arise to applicants or others skilled in the art. Accordingly, the appended claims as filed and as they may be amended are intended to embrace all such alternatives, modifications variations, improvements, and substantial equivalents.

What is claimed is:

1. A method of vaccinating a subject against a herpes simplex virus-2 (HSV-2) infection or a disease caused by an HSV-2 infection comprising administering to the subject an effective amount of a HSV-2 single-cycle virus and an effective amount of a recombinant HSV-2 glycoprotein D (rgD-2) to vaccinate the subject for the HSV-2 infection or the disease caused by the HSV-2 infection or the disease caused by the HSV-2 infection,
wherein the HSV-2 single-cycle virus comprises a genome having a deletion of glycoprotein D-encoding gene (gD-2) and said HSV-2 single-cycle virus is phenotypically complemented with an HSV-1 glycoprotein D (gD-1) on a lipid bilayer of said HSV-2 single-cycle virus.

2. The method of claim 1, wherein the administering of the HSV-2 single-cycle virus and the recombinant HSV-2 glycoprotein D occurs at substantially the same time.

3. The method of claim 1, wherein the HSV-2 single-cycle virus and the recombinant HSV-2 glycoprotein D are separately administered to the subject.

4. The method of claim 1, wherein the recombinant HSV-2 glycoprotein D is adjuvanted recombinant HSV-2 gD.

5. The method of claim 1, wherein the administering of the HSV-2 single-cycle virus occurs 1 second to 60 minutes before the administering of the recombinant HSV-2 glycoprotein D.

6. The method of claim 1, wherein the administering of the HSV-2 single-cycle virus occurs 1 second to 60 minutes after the administering of the recombinant HSV-2 glycoprotein D.

7. The method of claim 1, wherein the HSV-2 single-cycle virus is formulated for subcutaneous, intramuscular, intradermal, or intravaginal administration.

8. The method of claim 1, wherein the recombinant HSV-2 glycoprotein D is formulated for subcutaneous, intramuscular, or intradermal administration.

9. The method of claim 1, wherein the HSV-2 single-cycle virus and the recombinant HSV-2 glycoprotein D are administered by injection in a same limb of the subject.

10. The method of claim 1, wherein the HSV-1 glycoprotein D is not encoded for by the HSV-2 single-cycle virus, and said HSV-2 single-cycle virus is phenotypically complemented with the HSV-1 glycoprotein D by propagating the HSV-2 single-cycle virus in a complementing cell expressing the HSV-1 glycoprotein D.

11. A method of immunizing a subject against a herpes simplex virus-2 (HSV-2) infection or a disease caused by an HSV-2 infection comprising administering to the subject an effective amount of an HSV-2 single-cycle virus and an effective amount of a recombinant HSV-2 glycoprotein D (gD-2) to immunize the subject for the HSV-2 infection or the disease caused by the HSV-2 infection,
wherein the HSV-2 single-cycle virus comprises genome having a deletion of glycoprotein D-encoding gene (gD-2) and said HSV-2 single-cycle virus is phenotypically complemented with an HSV-1 glycoprotein D (gD-1) on a lipid bilayer of said HSV-2 single-cycle virus.

12. The method of claim 11, wherein the administering of the HSV-2 single-cycle virus and the recombinant HSV-2 glycoprotein D occurs at substantially the same time.

13. The method of claim 11, wherein the HSV-2 single-cycle virus and the recombinant HSV-2 glycoprotein D are separately administered to the subject.

14. The method of claim 11, wherein the recombinant HSV-2 glycoprotein D is adjuvanted recombinant HSV-2 gD.

15. The method of claim 11, wherein the administering of the HSV-2 single-cycle virus occurs 1 second to 60 minutes before the administering of the recombinant HSV-2 glycoprotein D.

16. The method of claim 11, wherein the administering of the HSV-2 single-cycle virus occurs 1 second to 60 minutes after the administering of the recombinant HSV-2 glycoprotein D.

17. The method of claim 11, wherein the HSV-2 single-cycle virus is formulated for subcutaneous, intramuscular, intradermal, or intravaginal administration.

18. The method of claim 11, wherein the recombinant HSV-2 glycoprotein D is formulated for subcutaneous, intramuscular, or intradermal administration.

19. The method of claim 11, wherein the HSV-2 single-cycle virus and the recombinant HSV-2 glycoprotein D are administered by injection in a same limb of the subject.

20. The method of claim 11, wherein the HSV-1 glycoprotein D is not encoded for by the HSV-2 single-cycle virus and said HSV-2 single-cycle virus is phenotypically complemented with the HSV-1 glycoprotein D by propagating the HSV-2 single-cycle virus in a complementing cell expressing the HSV-1 glycoprotein D.

21. A method of treating or inhibiting a herpes simplex virus-2 (HSV-2) infection in a subject or treating or inhibiting a disease caused by an HSV-2 infection in a subject, comprising administering to the subject an effective amount of an HSV-2 single-cycle virus and an effective amount of a recombinant HSV-2 glycoprotein D (gD-2) to treat or prevent the HSV-2 infection in the subject or the disease caused by the HSV-2 infection in the subject,
- wherein the HSV-2 single-cycle virus comprises a genome having a deletion of glycoprotein D-encoding gene (gD-2) and said HSV-2 single-cycle virus is phenotypically complemented with an HSV-1 glycoprotein D (gD-1) on a lipid bilayer of said HSV-2 single-cycle virus.

22. The method of claim 21, wherein the administering of the HSV-2 single-cycle virus and the recombinant HSV-2 glycoprotein D occurs at substantially the same time.

23. The method of claim 21, wherein the HSV-2 single-cycle virus and the recombinant HSV-2 glycoprotein D are separately administered to the subject.

24. The method of claim 21, wherein the recombinant HSV-2 glycoprotein D is adjuvanted recombinant HSV-2 gD.

25. The method of claim 21, wherein the administering of the HSV-2 single-cycle virus occurs 1 second to 60 minutes before the administering of the recombinant HSV-2 glycoprotein D.

26. The method of claim 21, wherein the administering of the HSV-2 single-cycle virus occurs 1 second to 60 minutes after the administering of the recombinant HSV-2 glycoprotein D.

27. The method of claim 21, wherein the HSV-2 single-cycle virus is formulated for subcutaneous, intramuscular, intradermal, or intravaginal administration.

28. The method of claim 21, wherein the recombinant HSV-2 glycoprotein D is formulated for subcutaneous, intramuscular, or intradermal administration.

29. The method of claim 21, wherein the HSV-2 single-cycle virus and the recombinant HSV-2 glycoprotein D are administered by injection in a same limb of the subject.

30. The method of claim 21, wherein the HSV-1 glycoprotein D is not encoded for by the HSV-2 single-cycle virus, and the HSV-2 single-cycle virus is phenotypically complemented with the HSV-1 glycoprotein D by propagating the HSV-2 single-cycle virus in a complementing cell expressing the HSV-1 glycoprotein D.

* * * * *

SEQUENCE LISTING

<160> NUMBER OF SEQ ID NOS: 3

<210> SEQ ID NO 1
<211> LENGTH: 27
<212> TYPE: DNA
<213> ORGANISM: Artificial sequence
<220> FEATURE:
<223> OTHER INFORMATION: Forward primer

<400> SEQUENCE: 1
tgcagtttac gtataaccac atacagc         27

<210> SEQ ID NO 2
<211> LENGTH: 17
<212> TYPE: DNA
<213> ORGANISM: Artificial sequence
<220> FEATURE:

```
<223> OTHER INFORMATION: Reverse primer

<400> SEQUENCE: 2
agcttgcggg cctcgtt                                                    17

<210> SEQ ID NO 3
<211> LENGTH: 22
<212> TYPE: DNA
<213> ORGANISM: Artificial sequence
<220> FEATURE:
<223> OTHER INFORMATION: Probe

<400> SEQUENCE: 3
cgccccagca tgtcgttcac gt                                              22
```